US009150647B2

(12) United States Patent
Mellstedt et al.

(10) Patent No.: US 9,150,647 B2
(45) Date of Patent: Oct. 6, 2015

(54) BIOLOGICAL INHIBITORS OF ROR1 CAPABLE OF INDUCING CELL DEATH

(75) Inventors: Hakan Mellstedt, Stockholm (SE); Hodjattallah Rabbani, Stockholm (SE); Ingrid Teige, Lund (SE)

(73) Assignee: Kancera AB, Solna (SE)

( * ) Notice: Subject to any disclaimer, the term of this patent is extended or adjusted under 35 U.S.C. 154(b) by 0 days.

(21) Appl. No.: 13/516,925

(22) PCT Filed: Dec. 10, 2010
(Under 37 CFR 1.47)

(86) PCT No.: PCT/EP2010/007524
§ 371 (c)(1),
(2), (4) Date: Mar. 1, 2013

(87) PCT Pub. No.: WO2011/079902
PCT Pub. Date: Jul. 7, 2011

(65) Prior Publication Data
US 2014/0004156 A1    Jan. 2, 2014

(30) Foreign Application Priority Data

Dec. 18, 2009 (GB) .................................. 0922143.3
Jun. 3, 2010 (GB) .................................. 1009307.8

(51) Int. Cl.
*A61K 39/395* (2006.01)
*C07K 16/28* (2006.01)
*C12N 15/113* (2010.01)
*A61K 39/00* (2006.01)

(52) U.S. Cl.
CPC .............. *C07K 16/28* (2013.01); *C07K 16/2803* (2013.01); *C12N 15/1137* (2013.01); *C12N 15/1138* (2013.01); *A61K 2039/505* (2013.01); *C07K 2317/34* (2013.01); *C07K 2317/73* (2013.01); *C07K 2317/732* (2013.01); *C12N 2310/14* (2013.01)

(58) Field of Classification Search
None
See application file for complete search history.

(56) References Cited

U.S. PATENT DOCUMENTS

| 4,440,859 | A | 4/1984 | Rutter et al. |
| 4,530,901 | A | 7/1985 | Weissmann |
| 4,582,800 | A | 4/1986 | Crowl |
| 4,677,063 | A | 6/1987 | Mark et al. |
| 4,678,751 | A | 7/1987 | Goeddel et al. |
| 4,704,362 | A | 11/1987 | Itakura et al. |
| 4,710,463 | A | 12/1987 | Murray |
| 4,757,006 | A | 7/1988 | Toole, Jr. et al. |
| 4,766,075 | A | 8/1988 | Goeddel et al. |
| 4,810,648 | A | 3/1989 | Stalker |
| 2012/0282177 | A1* | 11/2012 | Rohlff et al. ................. 424/1.49 |

FOREIGN PATENT DOCUMENTS

| WO | WO 98/16643 | 4/1998 |
| WO | WO 2005/100605 | 10/2005 |
| WO | WO 2007/146957 | 12/2007 |
| WO | WO 2008/076868 | 6/2008 |
| WO | WO 2010/124188 | 10/2010 |

OTHER PUBLICATIONS

Paganoni et al. Journal of Cell Science 118, 433-446 Published by The Company of Biologists 2005.*
International Search Report in International Application No. PCT/EP2010/007524, mailed Aug. 3, 2011, 7 pages.
International Preliminary Report on Patentability in International Application No. PCT/EP2010-007524, issued Jun. 19, 2012, 13 pages.
Better et al., "*Escherichia coli* Secretion of an Active Chimeric Antibody Fragment," *Science*, 1988, 240:1041.
Bird et al., "Single-Chain Antigen-Binding Proteins," *Science*, 1988, 242:423.
Cheson et al., "National Cancer Institute-sponsored Working Group guidelines for chronic lymphocytic leukemia: revised guidelines for diagnosis and treatment," *Blood*, 1996, 87:4990-4997.
Chiorazzi et al., "Chronic Lymphocytic Leukemia," *N Engl J Med*, 2005, 352:804-15.
Choudhury et al., "Silencing of ROR1 and FMOD with siRNA results in apoptosis of CLL cells," *Br J Haemotol.*, Aug. 31, 2010, 151(4):327-335.
Damle et al., "Ig V Gene Mutation status and CD38 Expression As Novel Prognostic Indicators in Chronic Lymphocytic Leukemia," *Blood*, 1999, 94:1840-7.
DaneshManesh et al., "Ror1, a cell surface receptor tyrosine kinase is expressed in chronic lymphocytic leukemia and may serve as a putative target for therapy," *Int'n J Cancer*, Sep. 1, 2008, 123(5):1190-1195.
Derossi et al., "Trojan peptides: the penetratin system for intracellular delivery," *Trends Cell Biol.*, 1998, 8:84-87.
Glass et al., "Agrin Acts via a MuSK Receptor Complex," *Cell*, 1996, 85:513-23.
Hamblin et al., "Unmutated Ig $V_H$ Genes are Associated with a More Aggressive Form of Chronic Lymphocytic Leukemia," *Blood*, 1999, 94:1848-54.
Heaney et al., "Soluble Receptors in Human Disease," *J Leukocyte Biol.*, Aug. 1, 1998, 64(2):135-146.
Huston et al., "Protein engineering of antibody binding sites: Recover of specific activity in an anti-digoxin single-chain Fv analogue produced in *Escherichia coli*,"*Proc. Natl. Acad. Sci. USA*, 1988, 85:5879.
Klein et al., "Gene Expression Profiling of B Cell Chronic Lymphocytic leukemia Reveals a Homogeneous Phenotype Related to Memory B Cells," *J Exp Med.*, 2001, 194:1625-38.

(Continued)

*Primary Examiner* — Michael Pak
(74) *Attorney, Agent, or Firm* — Fish & Richardson P.C.

(57) ABSTRACT

The invention relates to antibodies and siRNA molecules for inducing cell death by the specific binding of ROR1, domains thereof of nucleotide molecules encoding ROR1. There are also provided methods involving and uses of the antibodies and siRNA molecules of the invention.

5 Claims, 25 Drawing Sheets

(56) References Cited

OTHER PUBLICATIONS

Figure 1:
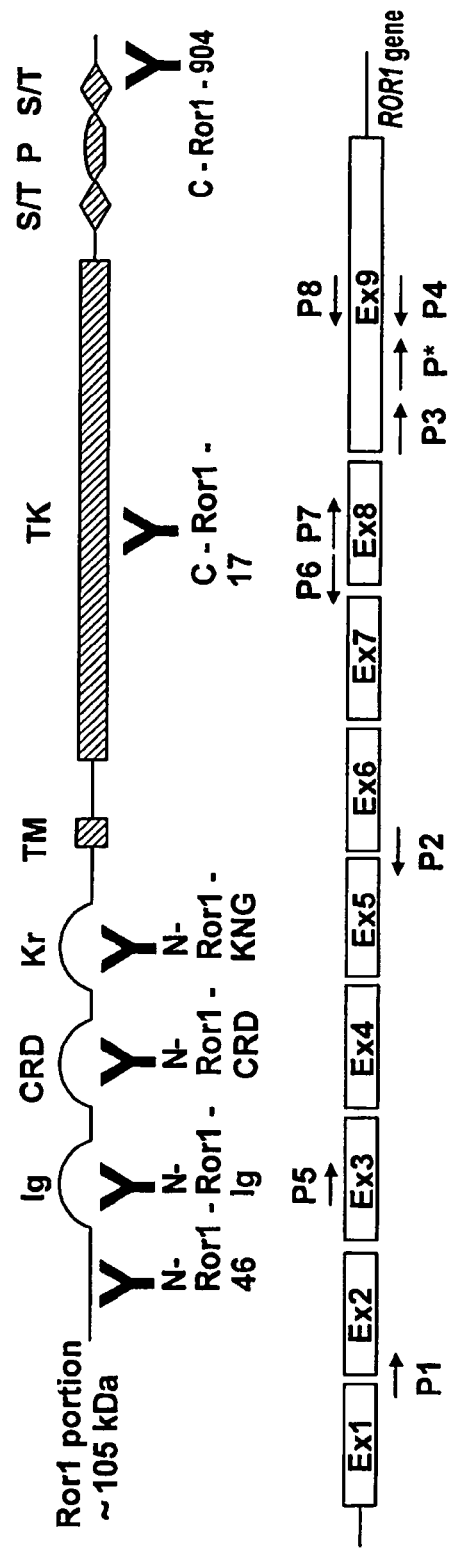

Kohler and Milstein, "Continuous cultures of fused cells secreting antibody of predefined specificity," *Nature*, 1975, 256:495-7.

Kokhaei P et al., "Telomerase (hTERT 611-626) serves as a tumor antigen in B-cell chronic lymphocytic leukemia and generates spontaneously antileukemic, cytotoxic T cells," Exp Hematol 2007;35:297-304.

Lapalombella et al., "Lenalidomide treatment promotes CD154 expression on CLL cells and enhances production of antibodies by normal B cells through a PI3-kinase-dependent pathway," Blood, Nov. 24, 2009, 115(3):2619-2629.

Lu et al., "Src Family Protein-tyrosine Kinases Alter the Function of PTEN to Regulate Phosphatidylinositol 3-Kinase/AKT Cascades," *J Biol Chem.*, 2003, 278:40057.

MacKeigan et al., "Sensitized RNAi screen of human kinases and phosphatases identifies new regulators of apoptosis and chemoresistance," Nature Cell Biol., Jun. 1, 2005, 7(6):591-600.

Masiakowski et al., "A Novel Family of Cell Surface Receptors with Tyrosine Kinase-like Domain," *J Biol Chem.*, 1992, 267:26181-90.

Mikaelsson et al, "Fibromodulin, an extracellular matrix protein: characterization of its unique gene and protein expression in B-cell chronic lymphocytic leukemia mantle cell lymphoma," *Blood*, 2005, 105:4828.

Morrison et al., "Chimeric human antibody molecules: Mouse antigen-binding domains with human constant region domains," *Proc. Natl. Acad. Sci. USA*, 1984, 81:6851-6855.

Reddy et al., "Human neural tissues express a truncated Ror1 receptor tyrosine kinase, lacking both extracellular and transmembrane domains," *Oncogene*, 1996, 13:1555-9.

Rezvany et al., "Autologous T lymphocytes may specifically recognize leukaemic B cells in patients with chronic lymphocytic leukaemia," *Br J Haematol.*, 2000, 111:608-17.

Rezvany et al., "Dendritic cells in patients have a normal non-progressive B-chronic lymphocytic leukaemia have a normal functional capability but abnormal cytokine patters," *Br J Haematol.*, 2001, 115:263-71.

Rosenwald et al., "Relation of Gene Expression Phenotype to Immunoglobulin Mutation Genotype in B Cell Chronic Lymphocytic Leukemia," *J Exp Med.*, 2001, 194:1639-47.

Saiki et al., "Primer-Directed Enzymatic Amplification of DNA with a Thermostable DNA Polymerase," *Science*, 1988, 239:487-491.

Skerra et al., "Assembly of a Functional Immunoglobulin Fv Fragment in *Escherichia coli*," *Science*, 1988, 240:1038.

Song et al., "RNA interference targeting Fas protects mice from fulminant hepatitia," *Nat. Med.*, 2003, 9:347-351.

Takayama et al., "Suppression of tumor angiogenesis and growth by gene transfer of a soluble form of vascular endothelial growth factor receptor into a remote organ," *Cancer Res.*, Apr. 15, 2000, 60(8):2169-2177.

Tyner et al., "RNAi screen for rapid therapeutic target identification in leukemia patients," *PNAS*, May 26, 2009, 106(21):8695-8700.

Valenzuela et al., "Receptor Tyrosine Kinase Specific for the Skeletal Muscle Lineage: Expression in Embryonic Muscle, at the Neuromuscular Junction, and after injury," *Neuron*, 1995, 15:573-84.

Ward et al., "Binding activities of a repertoire of single immunoglobulin variable domains secreted from *Escherichia coli*," *Nature*, 1989, 341:544.

Willems et al., "Consensus strategy to quantitate malignant cells in myeloma patients is validated in a multicenter study," *Belgium-Dutch Hematology-Oncology Group. Blood*, 2000, 96:63-70.

Wilkinson, "Immunochemical techniques inspire development of new antibody purification methods," The Scientist, vol. 14, No. 8 Apr. 17, 2000, pp. 25-28.

Winter et al., "Man-made antibodies," *Nature*, 1991, 349:293-299.

Yoda et al., "Expression and Functio of the Ror-Family Receptor Tyrosine Kinases During Development: Lessons from Genetic Analysis of Nematodes, Mice, and Humans," *J Recept Signal Transduct Res.*, 2003, 23:1-15.

Baskar et al., "Unique cell surface expression of receptor tyrosine kinase ROR1 in human B-cell chronic lymphocytic leukemia," Clin Cancer Res., Jan. 15, 2008, 14(2):396-404.

Chinese Office Action in Chinese Application No. 2010/800619632, mailed Aug. 27, 2013, 9 pages (translation included).

Daneshmanesh et al., "Monoclonal antibodies against ROR1 induce apoptosis of chronic lymphocytic leukemia (CLL) cells," Leukemia, 26(6):1348-55, Jun. 2012.

Daneshmanesh et al., "The PI3K/AKT/mTOR pathway is involved in direct apoptosis of CLL cells induced by ROR1 monoclonal antibodies," Br J Haematol., Nov. 19, 2014, 3 pages.

Essner et al., "RNA interference in adult mice," Nature (London), 2002, 418:38-39.

Fukada et al., "Antisera induced by infusions of autologous Ad-CD154-leukemia B cells identify ROR1 as an oncofetal, antigen and receptor for Wnt5a," PNAS USA, Feb. 26, 2008, 105(8):3047-3052.

Hojjat-Farsangi et al., "ReviewThe receptor tyrosine kinase ROR1—An oncofetal antigen for targetedcancer therapy," Semin Cancer Biol. 29:21-31; Dec. 2014.

\* cited by examiner

VL (kappa)

ATGGAAATTGAGATCACCCAGACTCCAGCACTCATGTCTGCATCTCCAGGGGAGAAGGTCAC
CATGACCTGCAGTGCCAGCTCAAGTGTAAGTTACATGTACTGGTACCAGCAGAAGCCAAGAT
CCTCCCCCAAACCCTGGATTTATCTCACATCCAACCTGGCTTCTGGAGTCCCTGCTCGCTTC
AGTGGCAGTGGGTCTGGGACCTCTTACTCTCTCACAATCAGCAGCATGGAGGCTGAAGATGC
TGCCACTTATTACTGCCAGCAGTGGAGTAGTAACCCGTACACGTTCGGAGGGGGGACCAGGC
TGGAGCTAAAA

```
atggaaattgagatcacccagactccagcactcatgtctgcatctccaggggagaaggtc
 M  E  I  E  I  T  Q  T  P  A  L  M  S  A  S  P  G  E  K  V
accatgacctgcagtgccagctcaagtgtaagttacatgtactggtaccagcagaagcca
 T  M  T  C  S  A  S  S  S  V  S  Y  M  Y  W  Y  Q  Q  K  P
agatcctcccccaaaccctggatttatctcacatccaacctggcttctggagtccctgct
 R  S  S  P  K  P  W  I  Y  L  T  S  N  L  A  S  G  V  P  A
cgcttcagtggcagtgggtctgggacctcttactctctcacaatcagcagcatggaggct
 R  F  S  G  S  G  S  G  T  S  Y  S  L  T  I  S  S  M  E  A
gaagatgctgccacttattactgccagcagtggagtagtaacccgtacacgttcggaggg
 E  D  A  A  T  Y  Y  C  Q  Q  W  S  S  N  P  Y  T  F  G  G
gggaccaggctggagctaaaa
 G  T  R  L  E  L  K
```

MEIEITQTPALMSASPGEKVTMTCSASSSVSYMYWYQQKPRSSPKPWIYLTSNLASG
VPARFSGSGSGTSYSLTISSMEAEDAATYYCQQWSSNPYTFGGGTRLELK

VH (VH2)

GAGGTCAAGCTGCAGCAGTCAGGACCTGAGCTGGTGAAGCCTGGGGCTTCAGTGAAG
ATATCCTGCAAGACTTCTGGATACACATTCACTGAATACACCATGCACTGGGTGAAG
CAGAGCCATGGAAAGAGCCTTGAGTGGATTGGAGGTATTAATCCTAACAATGGTGGT
ACTAGCTACAACCAGAAGTTCAAGGGCAAGGCCACATTGACTGTAGACAAGTCCTCC
AGCACAGCCTACATGGAGCTCCGCAGCCTGACATCTGAGGATTCTGCAGTCTATTAC
TGTGCTCTACAGGGGTTTGCTTACTGGGGCCAAGGGACTCCACTCACGGTCTCCTCA

```
gaggtcaagctgcagcagtcaggacctgagctggtgaagcctggggcttcagtgaagata
 E  V  K  L  Q  Q  S  G  P  E  L  V  K  P  G  A  S  V  K  I
tcctgcaagacttctggatacacattcactgaatacaccatgcactgggtgaagcagagc
 S  C  K  T  S  G  Y  T  F  T  E  Y  T  M  H  W  V  K  Q  S
catggaaagagccttgagtggattggaggtattaatcctaacaatggtggtactagctac
 H  G  K  S  L  E  W  I  G  G  I  N  P  N  N  G  G  T  S  Y
aaccagaagttcaagggcaaggccacattgactgtagacaagtcctccagcacagcctac
 N  Q  K  F  K  G  K  A  T  L  T  V  D  K  S  S  S  T  A  Y
atggagctccgcagcctgacatctgaggattctgcagtctattactgtgctctacagggg
 M  E  L  R  S  L  T  S  E  D  S  A  V  Y  Y  C  A  L  Q  G
tttgcttactggggccaagggactccactcacggtctcctca
 F  A  Y  W  G  Q  G  T  P  L  T  V  S  S
```

EVKLQQSGPELVKPGASVKISCKTSGYTFTEYTMHWVKQSHGKSLEWIGGINPNNGG
TSYNQKFKGKATLTVDKSSSTAYMELRSLTSEDSAVYYCALQGFAYWGQGTPLTVSS

Fig. 17

VL (kappa)

ATGGAAGTTCTGATCACCCAGACTCCATCCTCCTTATCTGCCTCTCTGGGAGAAAGAGTCAG
TCTCACTTGTCGGGCAAGTCAGGACATTGGTAGTAGCTTAAACTGGCTTCAGCAGGAACCAG
ATGGAACTATTAAACGCCTGATCTACGCCACATCCAGTTTAGATTCTGGTGTCCCCAAAAGG
TTCAGTGGCAGTAGGTCTGGGTCAGATTATTCTCTCACCATCAGCAGCCTTGAGTCTGAAGA
TTTTGTAGACTATTACTGTCTACAATATGCTAGTTCTCCGTACACGTTCGGAGGGGGGACCA
AACTGGAGCTCAAA

```
atggaagttctgatcacccagactccatcctccttatctgcctctctgggagaaagagtc
 M   E   V   L   I   T   Q   T   P   S   S   L   S   A   S   L   G   E   R   V
agtctcacttgtcgggcaagtcaggacattggtagtagcttaaactggcttcagcaggaa
 S   L   T   C   R   A   S   Q   D   I   G   S   S   L   N   W   L   Q   Q   E
ccagatggaactattaaacgcctgatctacgccacatccagtttagattctggtgtcccc
 P   D   G   T   I   K   R   L   I   Y   A   T   S   S   L   D   S   G   V   P
aaaaggttcagtggcagtaggtctgggtcagattattctctcaccatcagcagccttgag
 K   R   F   S   G   S   R   S   G   S   D   Y   S   L   T   I   S   S   L   E
tctgaagattttgtagactattactgtctacaatatgctagttctccgtacacgttcgga
 S   E   D   F   V   D   Y   Y   C   L   Q   Y   A   S   S   P   Y   T   F   G
gggggaccaaactggagctcaaa
 G   G   T   K   L   E   L   K
```

MEVLITQTPSSLSASLGERVSLTCRASQDIGSSLNWLQQEPDGTIKRLIYATSSLDS
GVPKRFSGSRSGSDYSLTISSLESEDFVDYYCLQYASSPYTFGGGTKLELK

---

VH (VH2)

GAGGTCAAGCTGCAGGAGTCTGGAGCTGAACTGGCAAGACCTGGGGCCTCAGTGAAG
ATGTCCTGCAAGGCTTCTGGCTACACCTTTACTAGCTACACGATGCACTGGGTAAAA
CAGAGGCCTGGACAGGGTCTGGAATGGATTGGATACATTAATCCTAGCAGTGGATAT
ACTGAGTACAATCAGAAGTTCAAGGACAAGACCACATTGACTGCAGACAAATCCTCC
AGCACAGCCTACATGCAACTGAGCAGCCTGACATCTGGGGACTCTGCGGTCTATTAC
TGTGCAAGAAGGGTACTATGGTTACGACGCGGAGACTACTGGGGCCAAGGCACTATA
CTCACGGTCTCCGCA

```
gaggtcaagctgcaggagtctggagctgaactggcaagacctggggcctcagtgaagatg
 E   V   K   L   Q   E   S   G   A   E   L   A   R   P   G   A   S   V   K   M
tcctgcaaggcttctggctacacctttactagctacacgatgcactgggtaaaacagagg
 S   C   K   A   S   G   Y   T   F   T   S   Y   T   M   H   W   V   K   Q   R
cctggacagggtctggaatggattggatacattaatcctagcagtggatatactgagtac
 P   G   Q   G   L   E   W   I   G   Y   I   N   P   S   S   G   Y   T   E   Y
aatcagaagttcaaggacaagaccacattgactgcagacaaatcctccagcacagcctac
 N   Q   K   F   K   D   K   T   T   L   T   A   D   K   S   S   S   T   A   Y
atgcaactgagcagcctgacatctggggactctgcggtctattactgtgcaagaagggta
 M   Q   L   S   S   L   T   S   G   D   S   A   V   Y   Y   C   A   R   R   V
ctatggttacgacgcggagactactggggccaaggcactatactcacggtctccgca
 L   W   L   R   R   G   D   Y   W   G   Q   G   T   I   L   T   V   S   A
```

EVKLQESGAELARPGASVKMSCKASGYTFTSYTMHWVKQRPGQGLEWIGYINPSSGY
TEYNQKFKDKTTLTADKSSSTAYMQLSSLTSGDSAVYYCARRVLWLRRGDYWGQGTI
LTVSA

Fig. 18

VL (Kappa)

ATGGATGTTGTGGTGACTCCAGTCTCCTGCTTCCTTAGCTGTATCTCTGGGGCAGAGGGCCA
CCATCTCATACAGGGCCAGCAAAAGTGTCAGTACATCTGGCTATAGTTATATGCACTGGAAC
CAACAGAAACCAGGACAGCCACCCAGACTCCTCATCTATCTTGTATCCAACCTAGAATCTGG
GGTCCCTGCCAGGTTCAGTGGCAGTGGGTCTGGGACAGACTTCACCCTCAACATCCATCCTG
TGGAGGAGGAGGATGCTGCAACCTATTACTGTCAGCACATTAGGGAGCTTACACGTTCGGAG
GGGGGACCAGGCTGGAGCTAAAA

```
atggatgttgtggtgactccagtctcctgcttccttagctgtatctctggggcagagggc
 M  D  V  V  V  T  P  V  S  C  F  L  S  C  I  S  G  A  E  G
caccatctcatacagggccagcaaaagtgtcagtacatctggcta tagt tatatgcactg
 H  H  L  I  Q  G  Q  Q  K  C  Q  Y  I  W  L  -  L  Y  A  L
gaaccaacagaaaccaggacagccacccagactcctcatctatcttgtatccaaccta ga
 E  P  T  E  T  R  T  A  T  Q  T  P  H  L  S  C  I  Q  P  R
atctggggtccctgccaggttcagtggcagtgggtctgggacagacttcaccctcaacat
 I  W  G  P  C  Q  V  Q  W  Q  W  V  W  D  R  L  H  P  Q  H
ccatcctgtggaggaggaggatgctgcaacctattactgtcagcacat tag ggagcttac
 P  S  C  G  G  G  G  C  C  N  L  L  L  S  A  H  -  G  A  Y
acgttcggaggggggaccaggctggagctaaaa
 T  F  G  G  G  T  R  L  E  L  K
```

MDVVVTPVSCFLSCISGAEGHHLIQGQQKCQYIWL-LYALEPTETRTATQTPHLSCIQPR
IWGPCQVQWQWVWDRLHPQHPSCGGGGCCNLLLSAH-GAYTFGGGTRLELK

VH (VH1)

GAGGTCAAACTGCAGGAGTCTGGACCTGAGCTGGTAAAGCCTGGGGCTTCAGTGAAGATGTC
CTGCAAGGCTTCTGGATACACATTCACTAGCTATGTTATGCACTGGGTGAAGCAGAAGCCTG
GGCAGGGCCTTGAGTGGATTGGATATATTAATCCTTACAATGATGGTACTAAGTACAATGAG
AAGTTCAAAGGCAAGGCCACACTGACTTCAGACAAATCCTCCAGCACAGCCTACATGGAGCT
CAGCAGCCTGACCTCTGAGGACTCTGCGGTCTATTACTGTGCAAGATGGAAGATCTACTATG
GTAACTACGAGGACTACTGGGGCCAAGGCACTCCTCTCACTGTCTCCTCA

```
gaggtcaaactgcaggagtctggacctgagctggtaaagcctggggcttcagtgaagatg
 E  V  K  L  Q  E  S  G  P  E  L  V  K  P  G  A  S  V  K  M
tcctgcaaggcttctggatacacattcactagctatgttatgcactgggtgaagcagaag
 S  C  K  A  S  G  Y  T  F  T  S  Y  V  M  H  W  V  K  Q  K
cctgggcagggccttgagtggattggatatattaatccttacaatgatggtactaagtac
 P  G  Q  G  L  E  W  I  G  Y  I  N  P  Y  N  D  G  T  K  Y
aatgagaagttcaaaggcaaggccacactgacttcagacaaatcctccagcacagcctac
 N  E  K  F  K  G  K  A  T  L  T  S  D  K  S  S  S  T  A  Y
atggagctcagcagcctgacctctgaggactctgcggtctattactgtgcaagatggaag
 M  E  L  S  S  L  T  S  E  D  S  A  V  Y  Y  C  A  R  W  K
atctactatggtaactacgaggactactggggccaaggcactcctctcactgtctcctca
 I  Y  Y  G  N  Y  E  D  Y  W  G  Q  G  T  P  L  T  V  S  S
```

EVKLQESGPELVKPGASVKMSCKASGYTFTSYVMHWVKQKPGQGLEWIGYINPYNDGTKY
NEKFKGKATLTSDKSSSTAYMELSSLTSEDSAVYYCARWKIYYGNYEDYWGQGTPLTVSS

Fig. 19

SEQUENCE LISTING

<160> NUMBER OF SEQ ID NOS: 40

<210> SEQ ID NO 1
<211> LENGTH: 15
<212> TYPE: PRT
<213> ORGANISM: Artificial Sequence
<220> FEATURE:
<223> OTHER INFORMATION: Extracellular domain to which antibody binds

<400> SEQUENCE: 1

Trp Asn Ile Ser Ser Glu Leu Asn Lys Asp Ser Tyr Leu Thr Leu
1               5                   10                  15

<210> SEQ ID NO 2
<211> LENGTH: 23
<212> TYPE: PRT
<213> ORGANISM: Artificial Sequence
<220> FEATURE:
<223> OTHER INFORMATION: N-Ror1-Ig recognition site

<400> SEQUENCE: 2

Arg Ser Thr Ile Tyr Gly Ser Arg Leu Arg Ile Arg Asn Leu Asp Thr
1               5                   10                  15

Thr Asp Thr Gly Tyr Phe Gln
            20

<210> SEQ ID NO 3
<211> LENGTH: 15
<212> TYPE: PRT
<213> ORGANISM: Artificial Sequence
<220> FEATURE:
<223> OTHER INFORMATION: N-Ror1-CRD recognition site

<400> SEQUENCE: 3

Tyr Met Glu Ser Leu His Met Gln Gly Glu Ile Glu Asn Gln Ile
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: N-Ror1-KNG recognition site

<400> SEQUENCE: 4

Cys Gln Pro Trp Asn Ser Gln Tyr Pro His Thr His Thr Phe Thr Ala
1               5                   10                  15

Leu Arg Phe Pro
            20

<210> SEQ ID NO 5
<211> LENGTH: 15
<212> TYPE: PRT
<213> ORGANISM: Artificial Sequence
<220> FEATURE:
<223> OTHER INFORMATION: N-Ror1-904 recognition site

<400> SEQUENCE: 5

Asn Lys Ser Gln Lys Pro Tyr Lys Ile Asp Ser Lys Gln Ala Ser
1               5                   10                  15

<210> SEQ ID NO 6
<211> LENGTH: 20
<212> TYPE: DNA
<213> ORGANISM: Artificial Sequence

```
<220> FEATURE:
<223> OTHER INFORMATION: ROR1 siRNA target sequence

<400> SEQUENCE: 6
atgaaccaat gaataacatc                                                    20

<210> SEQ ID NO 7
<211> LENGTH: 21
<212> TYPE: RNA
<213> ORGANISM: Artificial Sequence
<220> FEATURE:
<223> OTHER INFORMATION: ROR1 siRNA sequence

<400> SEQUENCE: 7
aaugaaccaa ugaauaacau c                                                  21

<210> SEQ ID NO 8
<211> LENGTH: 21
<212> TYPE: DNA
<213> ORGANISM: Artificial Sequence
<220> FEATURE:
<223> OTHER INFORMATION: ROR2 siRNA target sequence

<400> SEQUENCE: 8
aaaaatctat aaaggccatc t                                                  21

<210> SEQ ID NO 9
<211> LENGTH: 21
<212> TYPE: RNA
<213> ORGANISM: Artificial Sequence
<220> FEATURE:
<223> OTHER INFORMATION: ROR2 siRNA sequence

<400> SEQUENCE: 9
aaaaaucuau aaaggccauc u                                                  21

<210> SEQ ID NO 10
<211> LENGTH: 20
<212> TYPE: DNA
<213> ORGANISM: Artificial Sequence
<220> FEATURE:
<223> OTHER INFORMATION: ROR3 siRNA target sequence

<400> SEQUENCE: 10
acatgtcaat tccaaatcat                                                    20

<210> SEQ ID NO 11
<211> LENGTH: 21
<212> TYPE: RNA
<213> ORGANISM: Artificial Sequence
<220> FEATURE:
<223> OTHER INFORMATION: ROR3 siRNA sequence

<400> SEQUENCE: 11
aacaugucaa uuccaaauca u                                                  21

<210> SEQ ID NO 12
<211> LENGTH: 23
<212> TYPE: DNA
<213> ORGANISM: Artificial Sequence
<220> FEATURE:
<223> OTHER INFORMATION: t-Ror1 sense primer

<400> SEQUENCE: 12
ccaaaggacc ttctgcagtg gaa                                                23
```

```
<210> SEQ ID NO 13
<211> LENGTH: 26
<212> TYPE: DNA
<213> ORGANISM: Artificial Sequence
<220> FEATURE:
<223> OTHER INFORMATION: t-Ror1 antisense primer

<400> SEQUENCE: 13
tctcattcca gcactctgtc atgagg                                          26

<210> SEQ ID NO 14
<211> LENGTH: 20
<212> TYPE: DNA
<213> ORGANISM: Artificial Sequence
<220> FEATURE:
<223> OTHER INFORMATION: Ror1 RT-PCR sense primer

<400> SEQUENCE: 14
ctgctgccca agaaacagag                                                 20

<210> SEQ ID NO 15
<211> LENGTH: 23
<212> TYPE: DNA
<213> ORGANISM: Artificial Sequence
<220> FEATURE:
<223> OTHER INFORMATION: Ror1 RT-PCR antisense primer

<400> SEQUENCE: 15
catagtgaag gcagctgtga tct                                             23

<210> SEQ ID NO 16
<211> LENGTH: 24
<212> TYPE: DNA
<213> ORGANISM: Artificial Sequence
<220> FEATURE:
<223> OTHER INFORMATION: B-actin RT-PCR sense primer

<400> SEQUENCE: 16
attaaggaga agctgtgcta cgtc                                            24

<210> SEQ ID NO 17
<211> LENGTH: 24
<212> TYPE: DNA
<213> ORGANISM: Artificial Sequence
<220> FEATURE:
<223> OTHER INFORMATION: B-actin RT-PCR antisense primer

<400> SEQUENCE: 17
atgatggagt tgaaggtagt ttcg                                            24

<210> SEQ ID NO 18
<211> LENGTH: 26
<212> TYPE: DNA
<213> ORGANISM: Artificial Sequence
<220> FEATURE:
<223> OTHER INFORMATION: Ror1 RT-QPCR sense primer

<400> SEQUENCE: 18
aaagagctac ctctttctgc tgtacg                                          26

<210> SEQ ID NO 19
<211> LENGTH: 25
<212> TYPE: DNA
<213> ORGANISM: Artificial Sequence
<220> FEATURE:
<223> OTHER INFORMATION: Ror1 RT-QPCR antisense primer
```

```
<400> SEQUENCE: 19
cttcttgttg aaattccgtc cattg                                            25

<210> SEQ ID NO 20
<211> LENGTH: 27
<212> TYPE: DNA
<213> ORGANISM: Artificial Sequence
<220> FEATURE:
<223> OTHER INFORMATION: Ror1 RT-QPCR probe

<400> SEQUENCE: 20
catgctcagc tggttgctat caagacc                                          27

<210> SEQ ID NO 21
<211> LENGTH: 20
<212> TYPE: DNA
<213> ORGANISM: Artificial Sequence
<220> FEATURE:
<223> OTHER INFORMATION: B-actin RT-QPCR sense primer

<400> SEQUENCE: 21
cgacaggatg cagaaggaga                                                  20

<210> SEQ ID NO 22
<211> LENGTH: 20
<212> TYPE: DNA
<213> ORGANISM: Artificial Sequence
<220> FEATURE:
<223> OTHER INFORMATION: B-actin RT-QPCR antisense primer

<400> SEQUENCE: 22
cgtcatactc ctgcttgctg                                                  20

<210> SEQ ID NO 23
<211> LENGTH: 27
<212> TYPE: DNA
<213> ORGANISM: Artificial Sequence
<220> FEATURE:
<223> OTHER INFORMATION: B-actin RT-QPCR probe

<400> SEQUENCE: 23
aagatcaaga tcattgctcc tcctgag                                          27

<210> SEQ ID NO 24
<211> LENGTH: 28
<212> TYPE: DNA
<213> ORGANISM: Artificial Sequence
<220> FEATURE:
<223> OTHER INFORMATION: Ror1 RT-PCR extracellular domain sense primer

<400> SEQUENCE: 24
atgaataaca tcaccacgtc tctgggcc                                         28

<210> SEQ ID NO 25
<211> LENGTH: 24
<212> TYPE: DNA
<213> ORGANISM: Artificial Sequence
<220> FEATURE:
<223> OTHER INFORMATION: Ror1 RT-PCR extracellular domain antisense
      primer

<400> SEQUENCE: 25
ctccttggaa tcctttgaat cgca                                             24
```

-continued

```
<210> SEQ ID NO 26
<211> LENGTH: 20
<212> TYPE: DNA
<213> ORGANISM: Artificial Sequence
<220> FEATURE:
<223> OTHER INFORMATION: Ror1 RT-PCR kinase domain sense primer

<400> SEQUENCE: 26
ttcttcattt gcgtctgtcg                                                 20

<210> SEQ ID NO 27
<211> LENGTH: 20
<212> TYPE: DNA
<213> ORGANISM: Artificial Sequence
<220> FEATURE:
<223> OTHER INFORMATION: Ror1 RT-PCR kinase domain antisense primer

<400> SEQUENCE: 27
ctggctcggg aacatgtaat                                                 20

<210> SEQ ID NO 28
<211> LENGTH: 321
<212> TYPE: DNA
<213> ORGANISM: Artificial Sequence
<220> FEATURE:
<223> OTHER INFORMATION: VL sequence for Anti-Ror1 Ig24 (clone 2A4)
      antibody

<400> SEQUENCE: 28
atggaaattg agatcaccca gactccagca ctcatgtctg catctccagg ggagaaggtc     60
accatgacct gcagtgccag ctcaagtgta agttacatgt actggtacca gcagaagcca   120
agatcctccc ccaaaccctg gatttatctc acatccaacc tggcttctgg agtccctgct   180
cgcttcagtg gcagtgggtc tgggacctct tactctctca caatcagcag catggaggct   240
gaagatgctg ccacttatta ctgccagcag tggagtagta cccgtacac gttcggaggg    300 gggaccaggc tggagctaaa a                                             321

<210> SEQ ID NO 29
<211> LENGTH: 107
<212> TYPE: PRT
<213> ORGANISM: Artificial Sequence
<220> FEATURE:
<223> OTHER INFORMATION: VL sequence for Anti-Ror1 Ig24 (clone 2A4)
      antibody

<400> SEQUENCE: 29

Met Glu Ile Glu Ile Thr Gln Thr Pro Ala Leu Met Ser Ala Ser Pro
1               5                   10                  15

Gly Glu Lys Val Thr Met Thr Cys Ser Ala Ser Ser Val Ser Tyr
            20                  25                  30

Met Tyr Trp Tyr Gln Gln Lys Pro Arg Ser Ser Pro Lys Pro Trp Ile
        35                  40                  45

Tyr Leu Thr Ser Asn Leu Ala Ser Gly Val Pro Ala Arg Phe Ser Gly
    50                  55                  60

Ser Gly Ser Gly Thr Ser Tyr Ser Leu Thr Ile Ser Ser Met Glu Ala
65                  70                  75                  80

Glu Asp Ala Ala Thr Tyr Tyr Cys Gln Gln Trp Ser Ser Asn Pro Tyr
                85                  90                  95

Thr Phe Gly Gly Gly Thr Arg Leu Glu Leu Lys
            100                 105
```

```
<210> SEQ ID NO 30
<211> LENGTH: 342
<212> TYPE: DNA
<213> ORGANISM: Artificial Sequence
<220> FEATURE:
<223> OTHER INFORMATION: VH sequence for Anti-Ror1 Ig24 (clone 2A4)
      antibody

<400> SEQUENCE: 30
gaggtcaagc tgcagcagtc aggacctgag ctggtgaagc ctggggcttc agtgaagata      60
tcctgcaaga cttctggata cacattcact gaatacacca tgcactgggt gaagcagagc     120
catggaaaga gccttgagtg gattggaggt attaatccta acaatggtgg tactagctac     180
aaccagaagt tcaagggcaa ggccacattg actgtagaca gtcctccag cacagcctac      240 atggagctcc gcagcctgac atctgaggat tctgcagtct attactgtgc tctacagggg     300
tttgcttact ggggccaagg gactccactc acggtctcct ca                        342

<210> SEQ ID NO 31
<211> LENGTH: 114
<212> TYPE: PRT
<213> ORGANISM: Artificial Sequence
<220> FEATURE:
<223> OTHER INFORMATION: VH sequence for Anti-Ror1 Ig24 (clone 2A4)
      antibody

<400> SEQUENCE: 31

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Leu Gln Gly Phe Ala Tyr Trp Gly Gln Gly Thr Pro Leu Thr Val
            100                 105                 110

Ser Ser

<210> SEQ ID NO 32
<211> LENGTH: 324
<212> TYPE: DNA
<213> ORGANISM: Artificial Sequence
<220> FEATURE:
<223> OTHER INFORMATION: VL sequence for Anti-Ror1 CRD16 (clone 1C11)
      antibody

<400> SEQUENCE: 32
atggaagttc tgatcaccca gactccatcc tccttatctg cctctctggg agaaagagtc      60
agtctcactt gtcgggcaag tcaggacatt ggtagtagct aaactggct tcagcaggaa      120 ccagatggaa ctattaaacg cctgatctac gccacatcca gtttagattc tggtgtcccc     180
aaaaggttca gtggcagtag gtctgggtca gattattctc tcaccatcag cagccttgag     240
tctgaagatt ttgtagacta ttactgtcta caatatgcta gttctccgta cacgttcgga     300
gggggaccca aactggagct caaa                                             324
```

```
<210> SEQ ID NO 33
<211> LENGTH: 108
<212> TYPE: PRT
<213> ORGANISM: Artificial Sequence
<220> FEATURE:
<223> OTHER INFORMATION: VL sequence for Anti-Ror1 CRD16 (clone 1C11)
      antibody

<400> SEQUENCE: 33

Met Glu Val Leu Ile Thr Gln Thr Pro Ser Ser Leu Ser Ala Ser Leu
1               5                   10                  15

Gly Glu Arg Val Ser Leu Thr Cys Arg Ala Ser Gln Asp Ile Gly Ser
                20                  25                  30

Ser Leu Asn Trp Leu Gln Gln Glu Pro Asp Gly Thr Ile Lys Arg Leu
            35                  40                  45

Ile Tyr Ala Thr Ser Ser Leu Asp Ser Gly Val Pro Lys Arg Phe Ser
50                  55                  60

Gly Ser Arg Ser Gly Ser Asp Tyr Ser Leu Thr Ile Ser Ser Leu Glu
65                  70                  75                  80

Ser Glu Asp Phe Val Asp Tyr Tyr Cys Leu Gln Tyr Ala Ser Ser Pro
                85                  90                  95

Tyr Thr Phe Gly Gly Gly Thr Lys Leu Glu Leu Lys
            100                 105

<210> SEQ ID NO 34
<211> LENGTH: 357
<212> TYPE: DNA
<213> ORGANISM: Artificial Sequence
<220> FEATURE:
<223> OTHER INFORMATION: VH sequence for Anti-Ror1 CRD16 (clone 1C11)
      antibody

<400> SEQUENCE: 34
gaggtcaagc tgcaggagtc tggagctgaa ctggcaagac ctggggcctc agtgaagatg      60
tcctgcaagg cttctggcta cacctttact agctacacga tgcactgggt aaaacagagg     120
cctggacagg gtctggaatg gattggatac attaatccta gcagtggata tactgagtac     180
aatcagaagt tcaaggacaa gaccacattg actgcagaca atcctccag cacagcctac     240 atgcaactga gcagcctgac atctggggac tctgcggtct attactgtgc aagaagggta     300
ctatggttac gacgcggaga ctactggggc caaggcacta tactcacggt ctccgca       357

<210> SEQ ID NO 35
<211> LENGTH: 119
<212> TYPE: PRT
<213> ORGANISM: Artificial Sequence
<220> FEATURE:
<223> OTHER INFORMATION: VH sequence for Anti-Ror1 CRD16 (clone 1C11)
      antibody

<400> SEQUENCE: 35

Glu Val Lys Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Ser Ser Gly Tyr Thr Glu Tyr Asn Gln Lys Phe
50                  55                  60

Lys Asp Lys Thr Thr Leu Thr Ala Asp Lys Ser Ser Ser Thr Ala Tyr
65                  70                  75                  80
```

```
Met Gln Leu Ser Ser Leu Thr Ser Gly Asp Ser Ala Val Tyr Tyr Cys
                85                  90                  95

Ala Arg Arg Val Leu Trp Leu Arg Arg Gly Asp Tyr Trp Gly Gln Gly
            100                 105                 110

Thr Ile Leu Thr Val Ser Ala
        115

<210> SEQ ID NO 36
<211> LENGTH: 333
<212> TYPE: DNA
<213> ORGANISM: Artificial Sequence
<220> FEATURE:
<223> OTHER INFORMATION: VL sequence for Anti-Ror1 KNG20 (clone 4C10)
      antibody

<400> SEQUENCE: 36
atggatgttg tggtgactcc agtctcctgc ttccttagct gtatctctgg ggcagagggc      60
caccatctca tacagggcca gcaaaagtgt cagtacatct ggctatagtt atatgcactg    120
gaaccaacag aaaccaggac agccacccag actcctcatc tatcttgtat ccaacctaga    180
atctggggtc cctgccaggt tcagtggcag tgggtctggg acagacttca ccctcaacat    240
ccatcctgtg gaggaggagg atgctgcaac ctattactgt cagcacatta gggagcttac    300
acgttcggag gggggaccag gctggagcta aaa                                 333

<210> SEQ ID NO 37
<211> LENGTH: 109
<212> TYPE: PRT
<213> ORGANISM: Artificial Sequence
<220> FEATURE:
<223> OTHER INFORMATION: VL sequence for Anti-Ror1 KNG20 (clone 4C10)
      antibody

<400> SEQUENCE: 37

Met Asp Val Val Val Thr Pro Val Ser Cys Phe Leu Ser Cys Ile Ser
1               5                   10                  15

Gly Ala Glu Gly His His Leu Ile Gln Gly Gln Gln Lys Cys Gln Tyr
            20                  25                  30

Ile Trp Leu Leu Tyr Ala Leu Glu Pro Thr Glu Thr Arg Thr Ala Thr
        35                  40                  45

Gln Thr Pro His Leu Ser Cys Ile Gln Pro Arg Ile Trp Gly Pro Cys
    50                  55                  60

Gln Val Gln Trp Gln Trp Val Trp Asp Arg Leu His Pro Gln His Pro
65                  70                  75                  80

Ser Cys Gly Gly Gly Gly Cys Cys Asn Leu Leu Leu Ser Ala His Gly
                85                  90                  95

Ala Tyr Thr Phe Gly Gly Gly Thr Arg Leu Glu Leu Lys
            100                 105

<210> SEQ ID NO 38
<211> LENGTH: 360
<212> TYPE: DNA
<213> ORGANISM: Artificial Sequence
<220> FEATURE:
<223> OTHER INFORMATION: VH sequence for Anti-Ror1 KNG20 (clone 4C10)
      antibody

<400> SEQUENCE: 38
gaggtcaaac tgcaggagtc tggacctgag ctggtaaagc ctggggcttc agtgaagatg      60
tcctgcaagg cttctggata cacattcact agctatgtta tgcactgggt gaagcagaag    120
```

```
cctgggcagg gccttgagtg gattggatat attaatcctt acaatgatgg tactaagtac      180
aatgagaagt tcaaaggcaa ggccacactg acttcagaca aatcctccag cacagcctac      240
atggagctca gcagcctgac ctctgaggac tctgcggtct attactgtgc aagatggaag      300
atctactatg gtaactacga ggactactgg ggccaaggca ctcctctcac tgtctcctca      360

<210> SEQ ID NO 39
<211> LENGTH: 120
<212> TYPE: PRT
<213> ORGANISM: Artificial Sequence
<220> FEATURE:
<223> OTHER INFORMATION: VH sequence for Anti-Ror1 KNG20 (clone 4C10)
      antibody

<400> SEQUENCE: 39

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Trp Lys Ile Tyr Tyr Gly Asn Tyr Glu Asp Tyr Trp Gly Gln
            100                 105                 110

Gly Thr Pro Leu Thr Val Ser Ser
        115                 120

<210> SEQ ID NO 40
<211> LENGTH: 21
<212> TYPE: RNA
<213> ORGANISM: Artificial Sequence
<220> FEATURE:
<223> OTHER INFORMATION: ROR1 siRNA sequence

<400> SEQUENCE: 40
aaugaaccaa agaauaacau c                                               21
```

BIOLOGICAL INHIBITORS OF ROR1 CAPABLE OF INDUCING CELL DEATH

CROSS-REFERENCE TO RELATED APPLICATIONS

This application is a National Stage application under 35 U.S.C. §371 of International Application No. PCT/EP2010/007524, having an International Filing Date of Dec. 10, 2010, which claims the benefit of priority of Application No. GB 1009307.8, having a filing date of Jun. 3, 2010, and Application No. GB 0922143.3, having a filing date of Dec. 18, 2009, the disclosures of which are incorporated by reference in their entirety.

The present invention relates to biological molecules that inhibit ROR1. In particular there is provided inhibitors such as antibodies and siRNA molecules that are capable of inducing cell death by the specific binding of ROR1, domains thereof or nucleotide molecules encoding ROR1.

The work leading to this invention has received funding from the European Community's Seventh Framework Programme FP7/2007-2013/under grant agreement No HEALTH-F5-2008-200755.

Chronic lymphocytic leukaemia (CLL) is a white blood cell cancer that is characterised by an abnormal neoplastic proliferation of B lymphocyte cells (B cells). The B cells of CLL differ from normal B cells in their activation and maturation stage and are in particular derived from antigen experienced B cells with different immunoglobulin heavy chain variable (IgVH) gene mutations (Chiorazzi N et al., N Engl J Med 2005; 352:804-15). CLL patients with mutated IgVH genes have a better prognosis compared to patients with unmutated genes (Damle R N et al., Blood 1999; 94:1840-7; Hamblin T J et al., Blood 1999; 94:1848-54).

Global gene expression profiling studies have revealed partly distinguishing but in general overlapping expression profiles in mutated and unmutated leukaemic B cells, suggesting a common phenotype (Klein U et al., J Exp Med 2001; 194:1625-38; Rosenwald A et al., J Exp Med 2001; 194:1639-47).

Gene expression profiling studies have shown a 43.8 fold increase of the orphan receptor tyrosine kinase (RTK) ROR1 in CLL cells (Klein U et al., J Exp Med 2001; 194:1625-38). Ror1 is a member of the RTK family of orphan receptors related to muscle specific kinase (MUSK) and Trk neurotrophin receptors (Glass D J, et al., Cell 1996; 85:513-23; Masiakowski P et al., J Biol Chem 1992; 267:26181-90; Valenzuela D M et al., Neuron 1995; 15:573-84).

Ror receptors are cell surface receptors participating in signal transduction, cell-cell interaction, regulation of cell proliferation, differentiation, cell metabolism and survival (Masiakowski P et al., Biol Chem 1992; 267:26181-90; Yoda A et al., J Recept Signal Transduct Res 2003; 23:1-15). They are evolutionarily highly conserved between different species e.g. human, mouse, *Drosophila*, and *C. elegans*.

The human ROR1 gene has a coding region of 2814 bp with a predicted 937 amino acids sequence and 105 kDa protein size including an Ig-like domain, cysteine-rich domain, kringle domain, tyrosine kinase domain, and proline-rich domain (FIG. 1) (Yoda A et al., J Recept Signal Transduct Res 2003; 23:1-15).

Figure 2:
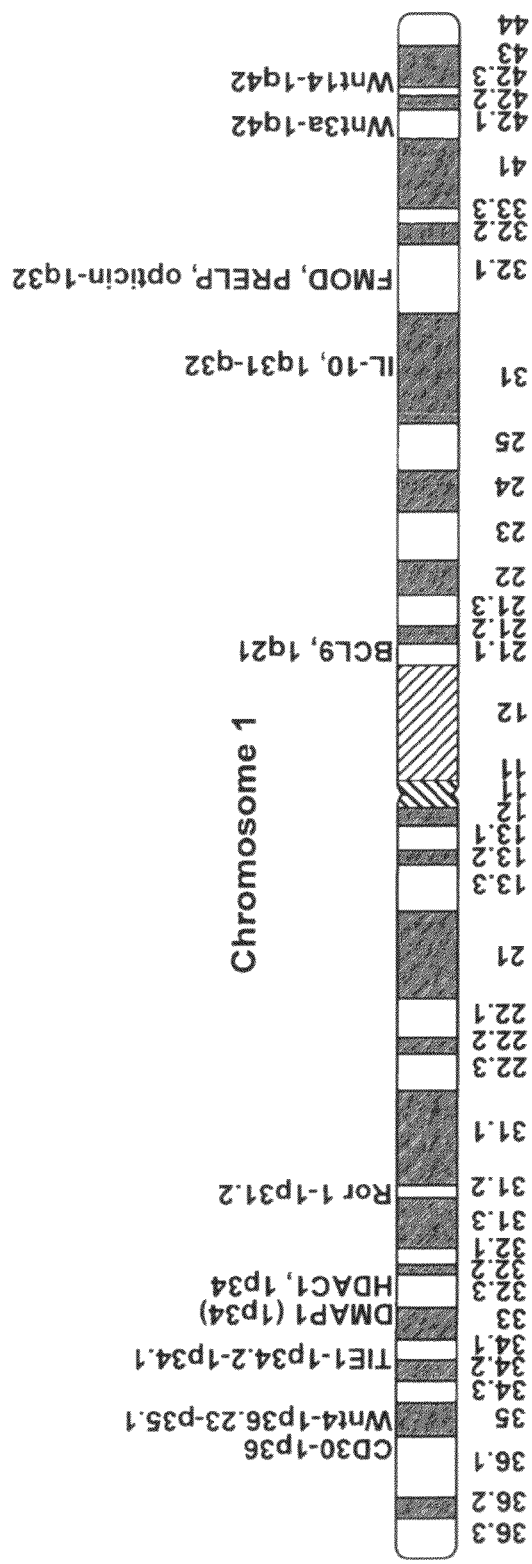

ROR1 is located on chromosomal region 1p31.3 (http://www.ensembl.org), a region where chromosomal aberrations are not frequently seen in haematological malignancies (FIG. 2). The human ROR1 is expressed in heart, lung, and kidney but less in placenta, pancreas and skeletal muscles (Reddy U R et al., Oncogene 1996; 13:1555-9). ROR1 was originally cloned from a neuroblastoma cell line (Masiakowski P et al., J Biol Chem 1992; 267:26181-90) and subsequently a shorter form lacking the entire extracellular domain but containing the transmembrane domain was isolated from a foetal brain library. Truncated Ror1 (t-Ror1) gene has been reported in foetal and adult human central nervous system, in human leukaemias, lymphoma cell lines, and in a variety of human cancers derived from neuroectoderm (Reddy U R et al., Oncogene 1996; 13:1555-9). A shorter transcript from exons 1-7 including a short part of intron 7 has also been described with a predicted length of 393 amino acids and a molecular weight of 44 kDa (Ensembl ID; ENSG00000185483).

In a first aspect of the invention there is provided a biological inhibitor of ROR1.

Biological inhibitors can take many forms and include differing modes of action. By Biological inhibition we mean that the amount of or action of ROR1 is reduced, and may be caused by exposure to a biological inhibitor. For example, the inhibitor may act directly by binding to ROR1 or a nucleotide sequence encoding ROR1. The inhibitor may alternatively act by preventing ROR1 interacting with molecules that it normally interacts with e.g. by blocking receptors, sequestering molecules that bind to or associate with ROR1, preventing insertion of ROR1 or its binders from inserting into a membrane, such as the cell membrane.

Preferably, the biological inhibitor binds specifically to either an extracellular domain of ROR1, an intracellular domain of ROR1 or to a nucleotide sequence encoding ROR1.

The biological inhibitor is conveniently one of an antibody, an interfering nucleic acid molecule or a soluble receptor.

In one embodiment the biological inhibitor is an antibody. By antibody we mean to complete antibodies and antigen binding fragments thereof. Such fragments are defined below.

Antibodies comprise two identical polypeptides of $M_r$ 50,000-70,000 (termed "heavy chains") that are linked together by a disulphide bond, each of which is linked to one of an identical pair of polypeptides of $M_r$ 25,000 (termed "light chains"). There is considerable sequence variability between individual N-termini of heavy chains of different antibody molecules and between individual light chains of different antibody molecules and these regions have hence been termed "variable domains". Conversely, there is considerable sequence similarity between individual C-termini of heavy chains of different antibody molecules and between individual light chains of different antibody molecules and these regions have hence been termed "constant domains".

The antigen-binding site is formed from hyper-variable regions in the variable domains of a pair of heavy and light chains. The hyper-variable regions are also known as complementarity-determining regions (CDRs) and determine the specificity of the antibody for a ligand. The variable domains of the heavy chain ($V_H$) and light chain ($V_L$) typically comprise three CDRs, each of which is flanked by sequence with less variation, which are known as framework regions (FRs).

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al., 1984, *Proc. Natl. Acad. Sci. USA*, 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al., 1988, *Science,* 240:1041). Fv molecules (Skerra et al., 1988, *Science,* 240, 1038); single-chain Fv (ScFv) molecules where the $V_H$ and $V_L$ partner domains are linked via a flexible oligopeptide (Bird et al., 1988, *Science* 242:423; Huston et al., 1988, *Proc. Natl. Acad. Sci. USA,* 85:5879) and single domain antibodies (dAbs) comprising isolated V domains (Ward et al., 1989 *Nature* 341, 544). A general review of the techniques involved in the synthesis of antibody fragments which retain their specific binding sites is to be found in Winter et al., 1991, *Nature,* 349, 293-299.

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface-active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants that can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen-binding site capable of immunoreacting with a particular epitope of the antigen characterized by a unique binding affinity for it.

The antibody may be a human or humanised antibody or fragment thereof.

The antibody may be a fragment including scFv molecules or Fab molecules.

By "ScFv molecules" we mean molecules wherein the $V_H$ and $V_L$ partner domains are linked via a flexible oligopeptide.

The advantages of using antibody fragments which have antigen-binding activity, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *Escherichia coli* (*E. coli*), thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site.

Methods for generating, isolating and using antibodies for a desired antigen or epitope are well known to those skilled in the relevant art. For example, an antibody may be raised in a suitable host animal (such as, for example, a mouse, rabbit or goat) using standard methods known in the art and either used as crude antisera or purified, for example by affinity purification. An antibody of desired specificity may alternatively be generated using well-known molecular biology methods, including selection from a molecular library of recombinant antibodies, or grafting or shuffling of complementarity-determining regions (CDRs) onto appropriate framework regions. Human antibodies may be selected from recombinant libraries and/or generated by grafting CDRs from non-human antibodies onto human framework regions using well-known molecular biology techniques.

Antibodies of one embodiment of the invention may possess the sequences shown in FIGS. 17, 18 and 19.

By extracellular domain we mean the part of a biological molecule that extends beyond the membrane surface of the cell, where said biological molecule is integrated in/embedded in the cell membrane. An example of such a biological molecule is a receptor which possess an extracellular portion to which ligands bind. If the polypeptide chain of the receptor crosses the bilayer several times, the external domain can comprise several "loops" sticking out of the membrane. Any one or combination of which may form a binding site for a ligand.

Preferably the extracellular domain to which the antibody binds has an amino acid sequence selected from:

```
                                        (SEQ ID NO: 1)
     WNISSELNKDSYLTL.

(SEQ ID NO: 2)
     RSTIYGSRLRIRNLDTTDTGYFQ.

(SEQ ID NO: 3)
     YMESLHMQGEIENQI (SEQ ID NO: 4)
     CQPWNSQYPHTHTFTALRFP
```

Alternatively the intracellular domain to which the antibody binds has the amino acid sequence NKSQKPYKIDSKQAS (SEQ ID NO:5).

Conveniently the antibody induces cell death in a cell expressing ROR1 upon specific binding of the antibody to an ROR1 molecule or domain thereof.

Preferably the biological inhibitor causes death of a cell expressing ROR1. By cell death we include all forms of cell death, including apoptosis, necrosis and autophagic cell death.

Apoptosis (programmed cell death, type I), is the process by which cells deliberately destroy themselves by systematically dismantling their contents which are then taken up by surrounding cells.

Autophagic cell death (also know as cytoplasmic or programmed cell death, type II) is characterised by characterized by the formation of large vacuoles which eat away organelles in a specific sequence prior to the nucleus being destroyed.

Necrosis is premature cell death that occurs without the controlled systematic dismantling of the cell and its constituent parts. Typically necrosis is characterised by rupturing of organelles and leakage of enzymatic compounds such as lysozymes which then damage and cause necrosis of neighbouring cells.

Antibodies may be used in therapy—for example, a medicament comprising therapeutic antibodies may be introduced into a subject to modulate the immune response of that subject. For example, a therapeutic antibody specific for an antigen in the subject will stimulate an immune response to that antigen, thereby inducing and/or promoting an immune response and aiding recovery. Methods for administering therapeutic antibodies to a patient in need thereof are well known in the art.

In an alternative embodiment the biological inhibitor may be an interfering nucleic acid molecule including siRNA, antisense RNA and dsRNA.

Preferably the interfering nucleic acid molecule is an antisense polynucleotide which is capable of hybridising to the nucleotide sequence encoding ROR1 or fragments or variants thereof.

Hybridisation may occur under any appropriate stringency conditions, for example 2×SSC at 65° C.

By "polynucleotide" we include single-stranded and/or double-stranded molecules of DNA (deoxyribonucleic acid) and/or RNA (ribonucleic acid) and derivatives thereof. By "encoding polynucleotide" we include a polynucleotide the sequence of which that may be translated to form a desired polypeptide.

It has now also been found that angiogenesis inhibition can be induced using siRNA (small interfering RNA molecules).

RNA interference (RNAi) is a natural mechanism for silencing specific genes. Genes provide cells with the instructions for making proteins, and when a gene is silenced, the cell stops making the protein specified by that gene. RNA interference was first observed in plants, but the first crucial breakthrough in understanding the RNAi mechanism came from studies of worms. This came in 1998 with the recognition that double-stranded RNA (dsRNA) played a pivotal role in RNAi. The first evidence for in vivo silencing of genes using siRNA was published 2002 (McCaffrey, A. P., Meuse, L., Pham, T. T., Conklin, D. S., Hannon, G. J. and Kay, M. A. (2002) RNA interference in adult mice. Nature (London) 418, 38-39) followed by the publication of Song et al. that showed that siRNA may be used for therapeutic intervention. This study showed that RNA interference targeting Fas protected mice from fulminant hepatitis. (Song, E., Lee, S. K., Wang, J. et al. (2003) Nat. Med. 9, 347-351).

siRNA molecules may be single-stranded (ss) or double-stranded (ds). The siRNA molecules may be delivered using a construct, which is capable of expressing the siRNA molecule upon delivery to the target cell.

A "small interfering RNA" or "short interfering RNA" or "siRNA" or "short hairpin RNA" or "shRNA" is a double-stranded RNA molecule that is complementary to a target nucleic acid sequence. A double-stranded RNA molecule is formed by the complementary pairing between a first RNA portion and a second RNA portion. The length of each portion generally is less than 30 nucleotides in length (e.g., 29, 28, 27, 26, 25, 24, 23, 22, 21, 20, 19, 18, 17, 16, 15, 14, 13, 12, 11, or 10 nucleotides). In some embodiments, the length of each portion is 19 to 25 nucleotides in length. In some siRNA molecules, the complementary first and second portions of the RNA molecule are the "stem" of a hairpin structure. The two portions can be joined by a linking sequence, which can form the "loop" in the hairpin structure. The linking sequence can vary in length. In some embodiments, the linking sequence can be 5, 6, 7, 8, 9, 10, 11, 12 or 13 nucleotides in length. A representative linking sequence is 5'-TTC AGA AGG-3', but any of a number of sequences can be used to join the first and second portions. The first and second portions are complementary but may not be completely symmetrical, as the hairpin structure may contain 3' or 5' overhang nucleotides (e.g., a 1, 2, 3, 4, or 5 nucleotide overhang).

RNA molecules have been shown by many researchers to be effective in suppressing mRNA accumulation. siRNA-mediated suppression of nucleic acid expression is specific as even a single base pair mismatch between siRNA and the targeted nucleic acid can abolish the action of RNA interference. siRNAs generally do not elicit anti-viral responses.

Conveniently, the siRNA is complementary to either a nucleotide sequence encoding an extracellular domain of ROR1 or a nucleotide sequence encoding an intracellular domain of ROR1.

Preferably the siRNA molecule has the siRNA sequence as shown in the table below:

| Target sequence (cDNA, 5'→3') | siRNA Sequence (5'→3') | siRNA name |
|---|---|---|
| AT GAA CCA ATG AAT AAC ATC (SEQ ID NO: 6) | AAU GAA CCA AUG AAU AAC AUC (SEQ ID NO: 7) | ROR 1 |
| AAA AAT CTA TAA AGG CCA TCT (SEQ ID NO: 8) | AAA AAU CUA UAA AGG CCA UCU (SEQ ID NO: 9) | ROR 2 |
| AC ATG TCA ATT CCA AAT CAT (SEQ ID NO: 10) | AAC AUG UCA AUU CCA AAU CAU (SEQ ID NO: 11) | ROR 3 |

In a second aspect of the invention there is provided a nucleotide sequence encoding a biological inhibitor of the first aspect.

The terms "nucleotide sequence" or "nucleic acid" or "polynucleotide" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

In a third aspect of the invention there is provided an expression vector containing a nucleotide sequence as described in the second aspect of the invention.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Methods well known to those skilled in the art can be used to construct expression vectors containing the coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or E. coli DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

In a fourth aspect of the invention there is provided a host cell comprising a nucleotide sequence or expression vector as described in the second and third aspects of the invention.

The DNA is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. Thus, the DNA insert may be operatively linked to an appropriate promoter. Bacterial promoters include the E. coli lacI and lacZ promoters, the T3 and T7 promoters, the gpt promoter, the phage X PR and PL promoters, the phoA promoter and the Up promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs will desirably also contain sites for transcription initiation and termination, and in the transcribed region, a ribosome binding site for translation. (WO 98/16643)

The vector is then introduced into the host through standard techniques. Generally, not all of the hosts will be transformed by the vector and it will therefore be necessary to select for transformed host cells. One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin resistance genes for culturing in E. coli and other bacteria. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

The polypeptide of the invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Many expression systems are known, including (but not limited to) systems employing: bacteria (eg. *E. coli* and *Bacillus subtilis*) transformed with, for example, recombinant bacteriophage, plasmid or cosmid DNA expression vectors; yeasts (eg. *Saccaromyces cerevisiae*) transformed with, for example, yeast expression vectors; insect cell systems transformed with, for example, viral expression vectors (eg. baculovirus); plant cell systems transfected with, for example viral or bacterial expression vectors; animal cell systems transfected with, for example, adenovirus expression vectors.

The vectors can include a prokaryotic replicon, such as the Col E1 ori, for propagation in a prokaryote, even if the vector is to be used for expression in other, non-prokaryotic cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

In a fifth aspect of the invention there is provided the use of a biological inhibitor as described in the first aspect of the invention in the induction of cell death.

In a sixth aspect of the invention there is provided a method of inducing cell death in one or more cells comprising exposing a cell expressing ROR1 to a biological inhibitor as described in the first aspect of the invention.

In a seventh aspect of the invention there is provided a biological inhibitor as described in the first aspect of the invention for use in medicine.

In an eighth aspect of the invention there is provided a biological inhibitor as described in the first aspect of the invention for use in treating Chronic Lymphocytic Leukaemia, Acute lymphocytic leukaemia, Acute myeloid leukaemia, non-Hodgkins lymphomas, chronic myeloid leukaemia, multiple myeloma, ovarian carcinoma, prostate cancer, breast cancer, melanoma, lung cancer, colorectal cancer, glioblastoma, pancreatic cancer and hepatocellular cancer.

By "treatment" we include the meanings that the number of cancer cells characterising the disease to be treated is reduced and/or further cancer cell growth is retarded and/or prevented and/or cancer cells are killed.

Chronic Lymphocytic Leuakemia can be identified using the criteria laid out in Example 1 which is based on the World Health Organisation classification of Neoplasms of Haemopoietic and lymphoid tissues.

In a ninth aspect of the invention there is provided the use of a biological inhibitor as described in the first aspect of the invention in the manufacture of a medicament for treating Chronic Lymphocytic Leukaemia, Acute lymphocytic leukaemia, Acute myeloid leukaemia, non-Hodgkins lymphomas, chronic myeloid leukaemia, multiple myeloma, ovarian carcinoma, prostate cancer, breast cancer, melanoma, lung cancer, colorectal cancer, glioblastoma, pancreatic cancer and hepatocellular cancer.

The biological inhibitors of the invention can be used to manufacture a pharmaceutical composition (medicament) that can be used to treat diseases such as Chronic Lymphocytic Leukaemia, Acute lymphocytic leukaemia, Acute myeloid leukaemia, non-Hodgkins lymphomas, chronic myeloid leukaemia, multiple myeloma, ovarian carcinoma, prostate cancer, breast cancer, melanoma, lung cancer, colorectal cancer, glioblastoma, pancreatic cancer and hepatocellular cancer.

In a tenth aspect of the invention there is provided a method of treating a disease comprising the step of administering to a subject a biological inhibitor as described in the first aspect of the invention, wherein the disease is selected from Chronic Lymphocytic Leukaemia, Acute lymphocytic leukaemia, Acute myeloid leukaemia, non-Hodgkins lymphomas, chronic myeloid leukaemia, multiple myeloma, ovarian carcinoma, prostate cancer, breast cancer, melanoma, lung cancer, colorectal cancer, glioblastoma, pancreatic cancer and hepatocellular cancer.

The term "subject" means all animals including humans. Examples of subjects include humans, cows, dogs, cats, goats, sheep, and pigs. The term "patient" means a subject having a disorder in need of treatment.

The disease to be treated may be progressive, i.e. that the disease worsens over time (i.e. is not stable or does not improve). In the case of CLL, patients are considered to have progressive disease if the following criteria were met: progression during the preceding 3 months in disease-related anaemia (haemoglobin <100 g/l), thrombocytopenia (<100× $10^9$/l) and/or an increase in spleen/liver/lymph-node size and/or more than a 2-fold increase in the blood lymphocyte count, if not the patients were considered non-progressive.

In an eleventh aspect of the invention there is provided a pharmaceutical composition comprising a biological inhibitor as described in the first aspect of the invention and a pharmaceutically acceptable excipient, diluent or carrier.

The examples describe some methods of producing pharmaceutical formulations, however the skilled person will appreciate that the most appropriate formulation will depend on a number of factors including route of administration, patient type (e.g. patient age, weight/size).

Preferably the pharmaceutical composition induces cell death in a cell expressing ROR1.

In a twelfth aspect of the invention there is provided a kit of parts comprising:
(i) a biological inhibitor as described in the first aspect of the invention or a pharmaceutical composition as described in the eleventh aspect of the invention;
(ii) apparatus for administering the antibody, siRNA or pharmaceutical composition; and
(iii) instructions for use.

EMBODIMENTS OF THE INVENTION

Embodiments of the invention are described in the following numbered paragraphs.
1. A biological inhibitor of ROR1.
2. A biological inhibitor as described in paragraph 1 wherein the inhibitor binds specifically to either an extracellular domain of ROR1, an intracellular domain of ROR1 or to an nucleotide sequence encoding ROR1.

3. A biological inhibitor as described in paragraph 1 or 2 wherein the inhibitor is selected from an antibody, interfering nucleic acid molecule or a soluble receptor.
4. A biological inhibitor as described in paragraph 3 wherein the antibody is a complete antibody or a fragment thereof.
5. A biological inhibitor as described in any previous paragraph wherein on specific binding to ROR1 or the nucleotide sequence encoding ROR1, the biological inhibitor induces cell death in a cell expressing ROR1.
6. A biological inhibitor as described in any of paragraphs 1 to 4 wherein the extracellular domain to which the biological inhibitor binds has the amino acid sequence WNISSELNKDSYLTL (SEQ ID NO: 1).
7. A biological inhibitor as described in any of paragraphs 1 to 4 wherein the intracellular domain to which the biological inhibitor binds has the amino A biological inhibitor as described in any of paragraphs 1 to 4 wherein the intracellular domain to which the biological inhibitor binds has the amino acid sequence NKSQKPYKIDSKQAS (SEQ ID NO:5).
8. A biological inhibitor as described in any of paragraphs 1 to 5 wherein the interfering nucleic acid molecule is an interfering RNA molecule such as a siRNA, an antisense RNA or a dsRNA.
9. A biological inhibitor as described in any of paragraphs 1 to 5 and 8 wherein the interfering nucleic molecule is complementary to the nucleotide sequence encoding ROR1 or fragments or variants thereof.
10. A biological inhibitor as described in paragraph 9 wherein the interfering nucleic acid is an antisense polynucleotide which is capable of hybridising to the nucleotide sequence encoding ROR1 or fragments or variants thereof.
11. A biological inhibitor as described in paragraph 9 or 10 wherein the interfering nucleic acid is complementary to either a nucleotide sequence encoding an extracellular domain of ROR1 or a nucleotide sequence encoding an intracellular domain of ROR1.
12. A biological inhibitor as described in any of paragraphs 5 to 7 wherein the interfering nucleic acid is an siRNA having a sequence selected from AAUGAACCAAAGAAUAACAUC (SEQ ID NO: 40), AAAAAUCUAUAAAGGCCAUCU (SEQ ID NO: 9) or AACAUGUCAAUUCCAAAUCAU (SEQ ID NO:11).
13. A nucleotide sequence encoding a biological inhibitor as described in any previous paragraph.
14. An expression vector containing a nucleotide sequence as described in paragraph 13.
15. A host cell comprising a nucleotide sequence or expression vector as described in paragraphs 13 or 14.
16. Use of a biological inhibitor as defined in paragraphs 1 to 12 in the induction of cell death of a cell.
17. A method of inducing cell death in one or more cells comprising exposing a cell expressing ROR1 to a biological inhibitor as defined in paragraphs 1 to 12.
18. A biological inhibitor as defined in paragraphs 1 to 12 for use in medicine.
19. A biological inhibitor as defined in paragraphs 1 to 12 for use in treating a disease selected from Chronic Lymphocytic Leukaemia, Acute lymphocytic leukaemia, Acute myeloid leukaemia, non-Hodgkin lymphomas, chronic myeloid, multiple myeloma, ovarian carcinoma, prostate cancer, breast cancer, melanoma, lung cancer, colorectal cancer, glioblastoma, pancreatic cancer and hepatocellular cancer.
20. Use of a biological inhibitor as defined in paragraphs 1 to 12 in the manufacture of a medicament for treating a disease selected from Chronic Lymphocytic Leukaemia, Acute lymphocytic leukaemia, Acute myeloid leukaemia, non-Hodgkin lymphomas, chronic myeloid, multiple myeloma, ovarian carcinoma, prostate cancer, breast cancer, melanoma, lung cancer, colorectal cancer, glioblastoma, pancreatic cancer and hepatocellular cancer.
21. A method of treating a disease comprising the step of administering to a subject a biological inhibitor as claimed in paragraphs 1 to 12, wherein the disease is selected from Chronic Lymphocytic Leukaemia, Acute lymphocytic leukaemia, Acute myeloid leukaemia, non-Hodgkin lymphomas, chronic myeloid, multiple myeloma, ovarian carcinoma, prostate cancer, breast cancer, melanoma, lung cancer, colorectal cancer, glioblastoma, pancreatic cancer and hepatocellular cancer.
22. A biological inhibitor, use or method as claimed in paragraphs 19 to 21 wherein the disease is progressive.
23. A biological inhibitor, use or method as claimed in paragraphs 19 to 22 wherein the disease is Chronic Lymphocytic Leukaemia.
24. A pharmaceutical composition comprising a biological inhibitor as defined in paragraphs 1 to 12 and a pharmaceutically acceptable excipient, diluent or carrier.
25. A pharmaceutical composition as claimed in claim 18 which induces cell) death in a cell expressing ROR1.
26. A kit of parts comprising:
    (i) a biological inhibitor as claimed in paragraphs 1 to 12 or a pharmaceutical composition as claimed in paragraphs 24 or 25;
    (ii) apparatus for administering the biological inhibitor or pharmaceutical composition; and
    (iii) instructions for use.
27. A biological inhibitor substantially as described herein with reference to the examples and figures.
28. A use of a biological inhibitor substantially as described herein with reference to the examples and figures.
29. A method using a biological inhibitor substantially as described herein with reference to the examples and figures.
30. A pharmaceutical composition substantially as described herein with reference to the examples and figures.
31. A kit of parts substantially as described herein with reference to the examples and figures.

EXAMPLES

The following examples embody various aspects of the invention. It will be appreciated that the specific antibodies and/or antigens used in the examples serve to illustrate the principles of the invention and are not intended to limit its scope.

The following examples are described with reference to the accompanying figures in which:

FIG. 1—Schematic presentation of the ROR1 gene and the Ror1 protein.

The human ROR-1 gene has a coding region of 2814 bp which predicted 937 amino acids sequence and 105 kDa protein size including an Ig-like domain, cysteine-rich domain, kringle domain, tyrosine kinase domain, and pro-line-rich domain.

Positions of antibody recognition sites of N-Ror1-Ig (RSTIYGSRLRIRNLDTTDTGYFQ, SEQ ID NO:2), N-Ror1-CRD (YMESLHMQGEIENQI, SEQ ID NO:3), NRor1-KNG (CQPWNSQYPHTHTFTALRFP, SEQ ID NO:4), C-Ror1-17, C-Ror1-904 (NKSQKPYKIDSKQAS, SEQ ID NO:5) (Y) as well as the protein domains:

Immunoglobulin like domain (Ig), cysteine rich domain (CRD), Kringle domain (Kr), transmembrane domain (TM), tyrosine kinase domain (TK), serine and threonine rich domain (S/T), and proline rich domain (P) are indicated.

FIG. 2—Map of human chromosome 1 indicating part of the genes overexpressed in B-CLL.

Figure 3:
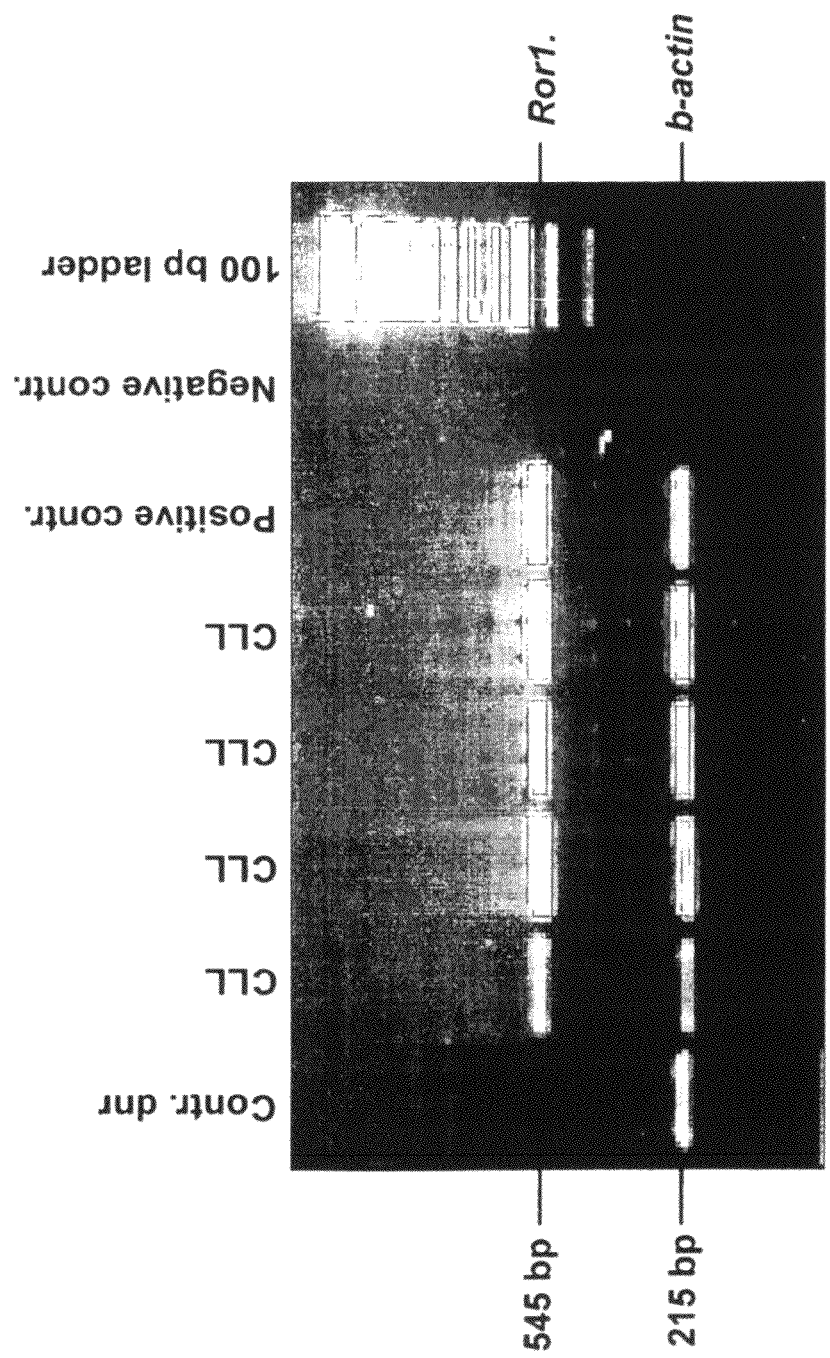

FIG. 3—ROR1 gene expression (RT-PCR) in CLL cells vs control donor

Positive control=PCR product cloned into pGEM-T easy vector

Negative control=reaction mixture without template

Figure 4:
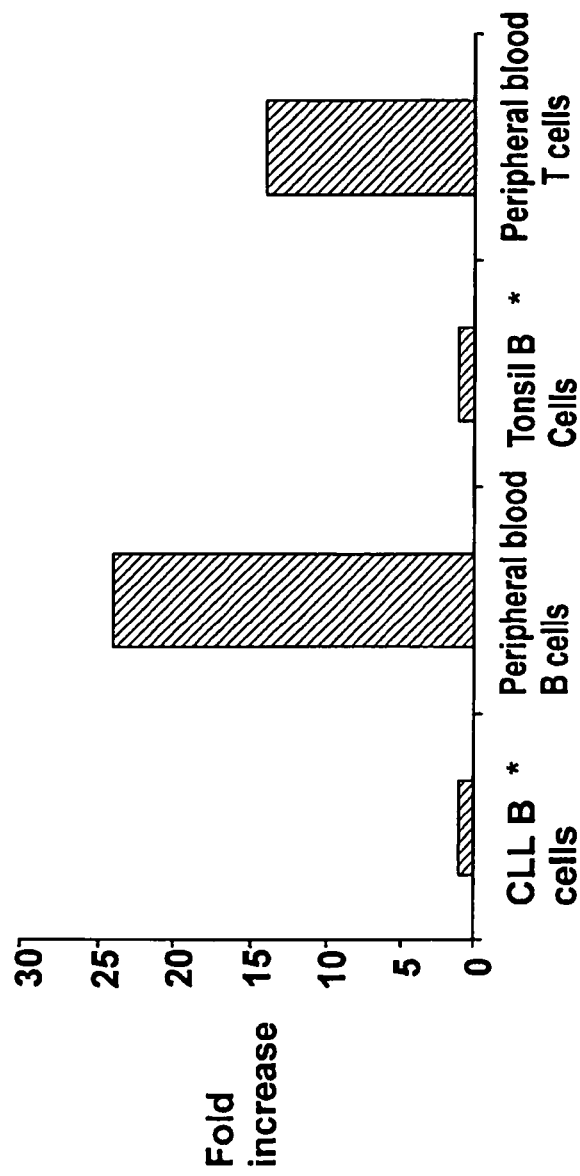

FIG. 4—ROR1 gene expression: PMA/ionomycin is required to induce expression in normal lymphocytes A representative example of Ror1 expression in activated (PMA/ionomycin) normal B and T lymphocytes, tonsil B cells and leukaemic CLL cells after 48 h of culture. The expression was determined by quantitative real-time PCR. Fold increase was related to the level observed at time zero. CLL cells and tonsil B cells, which constitutively express Ron mRNA could not be further activated, while the strong activation signal induced gene expression of Rod in normal B and T cells.

Figure 5:
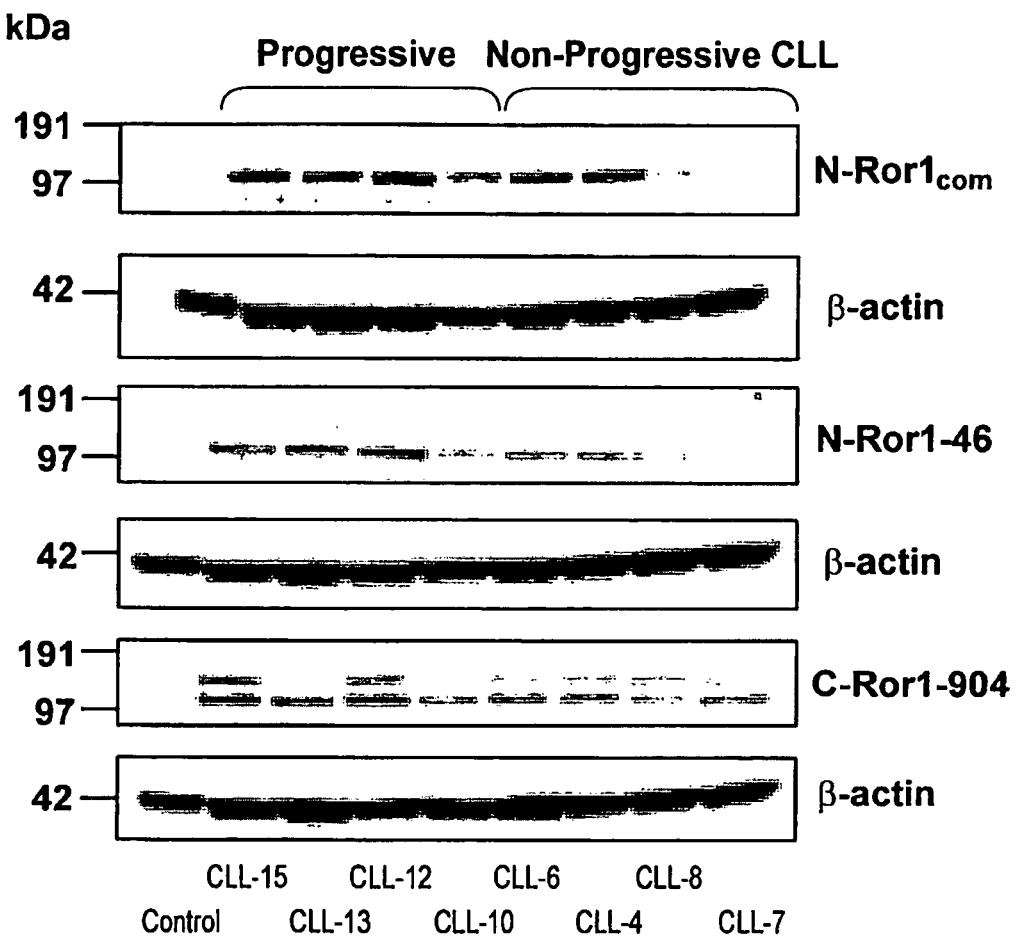

*=CLL cells and tonsil B cells constitutively expressed ROR1 and could not be further activated FIG. 5—Ror1 protein expression in CLL cells and healthy controls (Western blot)

All three antibodies showed a 105 kD band. C-Ror-1-904 also detected an estimated 130 kDA variant of Ror-1. The blots were stripped and stained with a beta-actin antibody to show the intriguity of the loaded samples.

Figure 6:
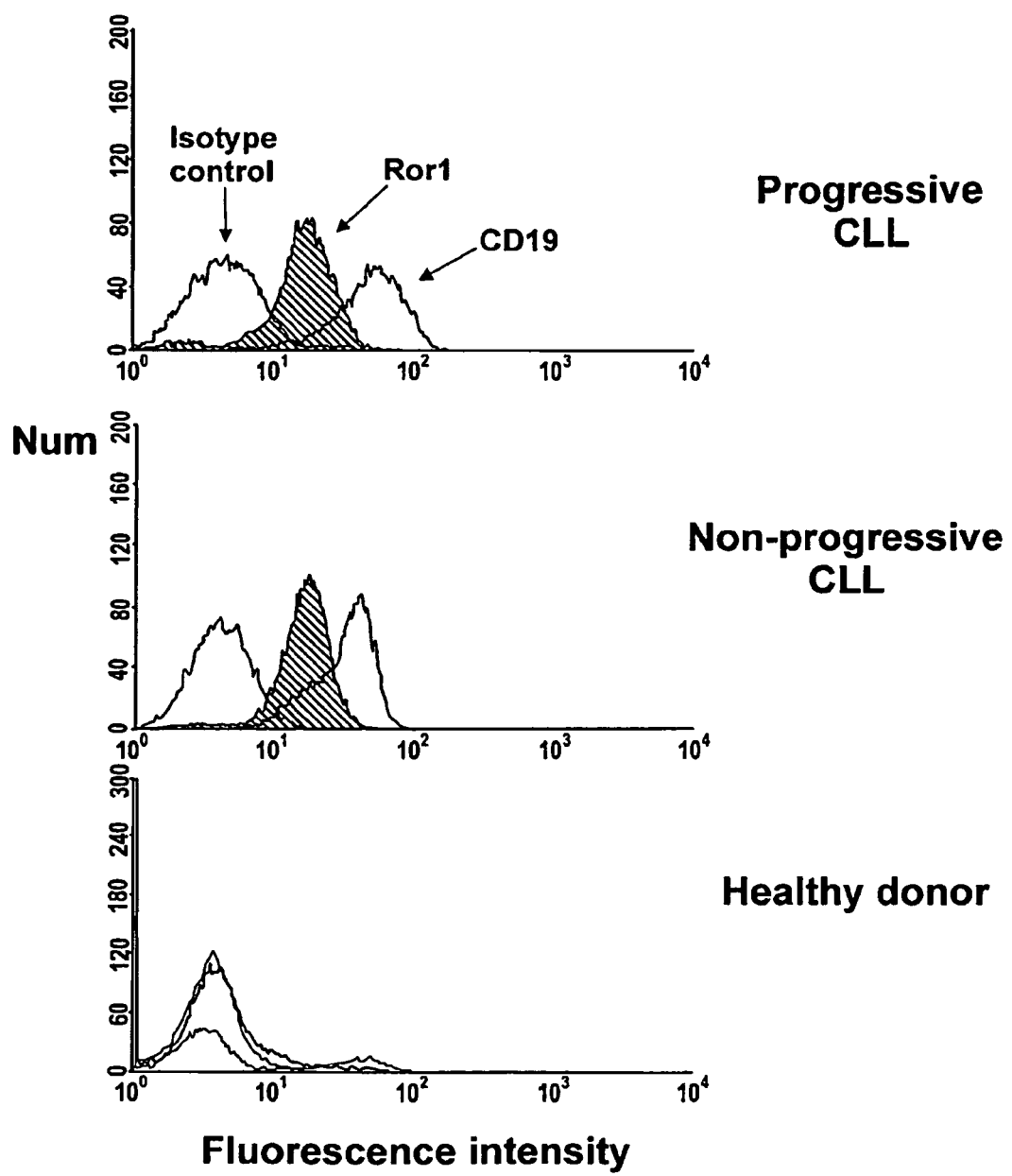

FIG. 6—Cell surface staining intensity for Ror1 compared to CD19 in two CLL patients and a healthy donor Shows cell surface staining for Ror1 (M-Ror-1$_{com}$) and CD19 of leukaemic cells from progressive and non-progressive CLL patients as well as PBMC of a healthy donor.

Figure 7:
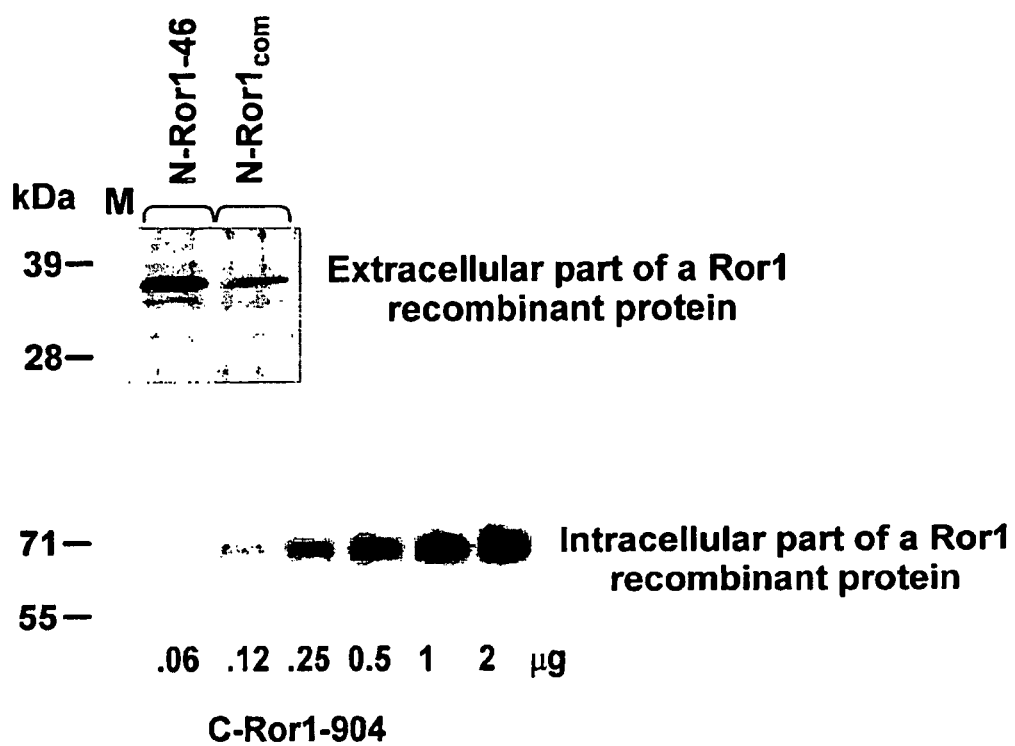

FIG. 7—Specificity control of the polyclonal antibodies.

Upper panel: Western blot analyses using a commercially available anti-Ror-1 polyclonal antibody (N-Ror-1$_{com}$). Both antibodies react with the same 37 kDA band. The recombinant extracellular part of the Ror-1 protein was expressed in E. coli and supernatant concentrated 30×.

Lower panel: Western blot using a serially diluted commercially available recombinant Ror-1 protein representing a cytoplasmic region and probed with our rabbit polyclonal antibody c-Ror-1-904. [The Ror-c-1-904 antibody did not react with the recombinant extra cellular part of the Ror-1 protein (data not shown)].

Figure 8:
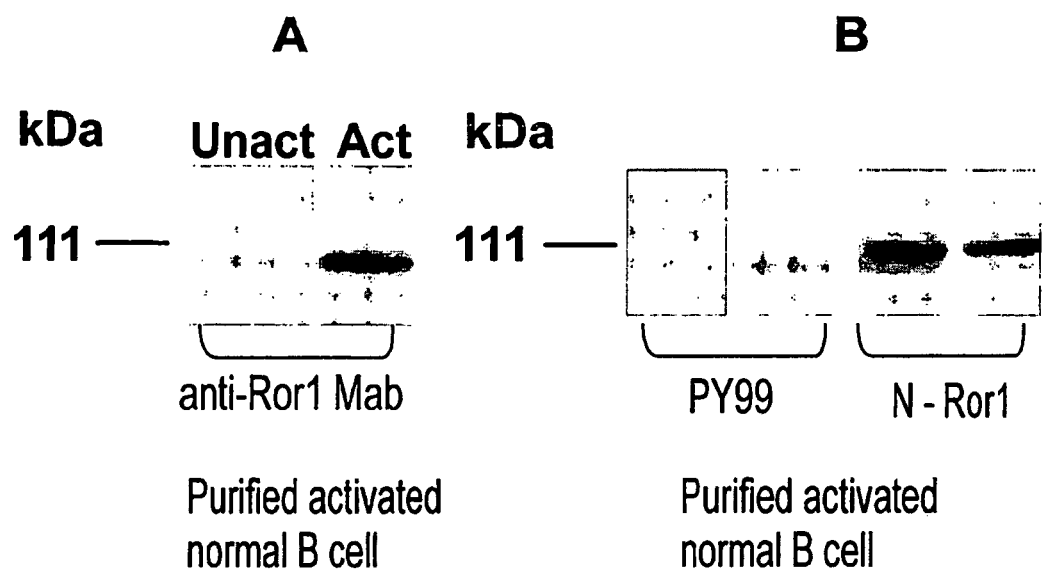

FIG. 8—Ror1 protein in activated normal B cell is not phosphorylated

PMA/ionomycin activation of normal B cells induced expression of the Ror-1 protein which is not phosphorylated.

Panel A=Immunoblotting of cell lysates of purified normal peripheral B cells activated with PMA/ionomycin and probed with anti-Ror1 Mab Panel B=Immunoprecipitation (using anti-Ror1 Mab) of purified normal blood B cells activated with PMA/ionomycin, treated without (−) or with (+) perveanadate (pos control, to induce phosphorylation), stained with PY99 monoclonal antibody and reprobed with N—ROr1.

PMA/ionomycin activated B cells did not show any autophosphorylation.

Figure 9:
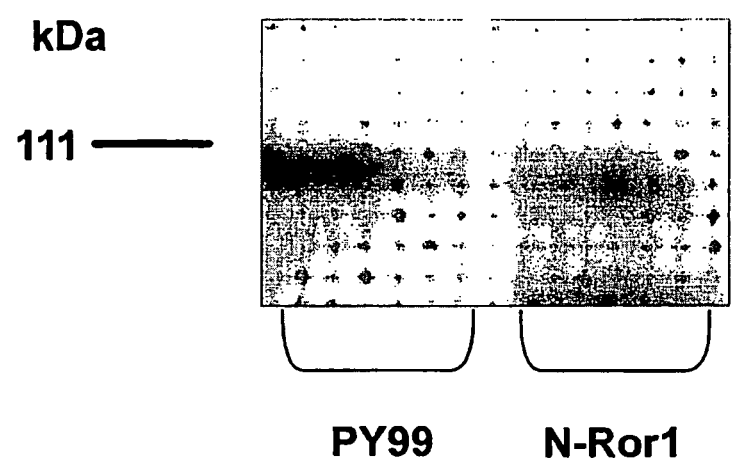

FIG. 9—The Ron protein is constitutively phosphorylated in CLL cells.

A representative experiment of a CLL patient. Immunoblotting performed for protein phosphorylation using a phosphotyrosine monoclonal antibody (PY99). Cell lysates were subjected to immunoprecipitation with an anti-Ror1 monoclonal antibody. The PY99 antibody was used for probing of phosphorylation with subsequent stripping and reprobing with the N-Ror1 polyclonal antibody.

Figure 10:
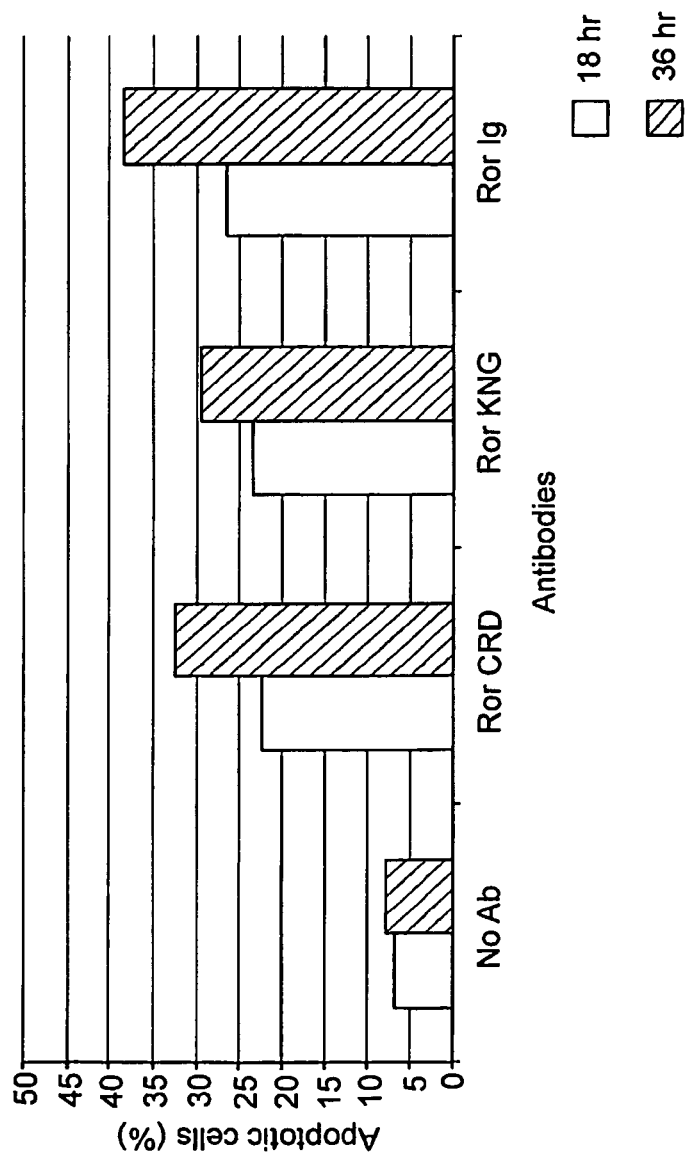

FIG. 10—Anti-Ror1 monoclonal antibodies induced Apoptosis (Annexin-V/PI) of CLL cells (CLL patient no. 1)

Anti Ror-1 monoclonal antibodies against the external domain of the Ror-1 receptor induce apoptosis of CLL cells. The pattern of apoptosis varied between patients.

CRD=cysteine-rich domain KNG=kringle domain; Ig=immunoglobulin domain

Figure 11:
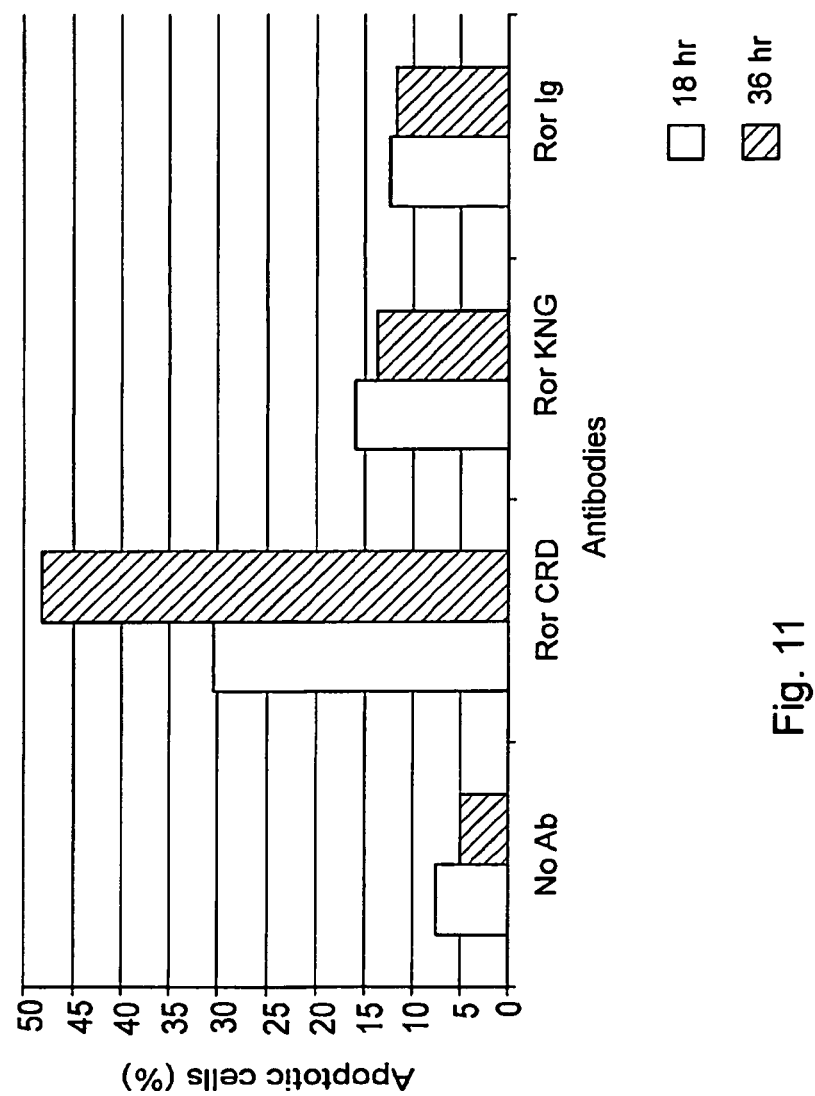

FIG. 11—Anti-Rod monoclonal antibodies induced Apoptosis (Annexin-V/PI) of CLL cells (CLL patient no. 2)

Anti Ror-1 monoclonal antibodies against the external domain of the Ror-1 receptor induce apoptosis of CLL cells. The pattern of apoptosis varied between patients.

CRD=cysteine-rich domain KNG=kringle domain; Ig=immunoglobulin domain

Figure 12:
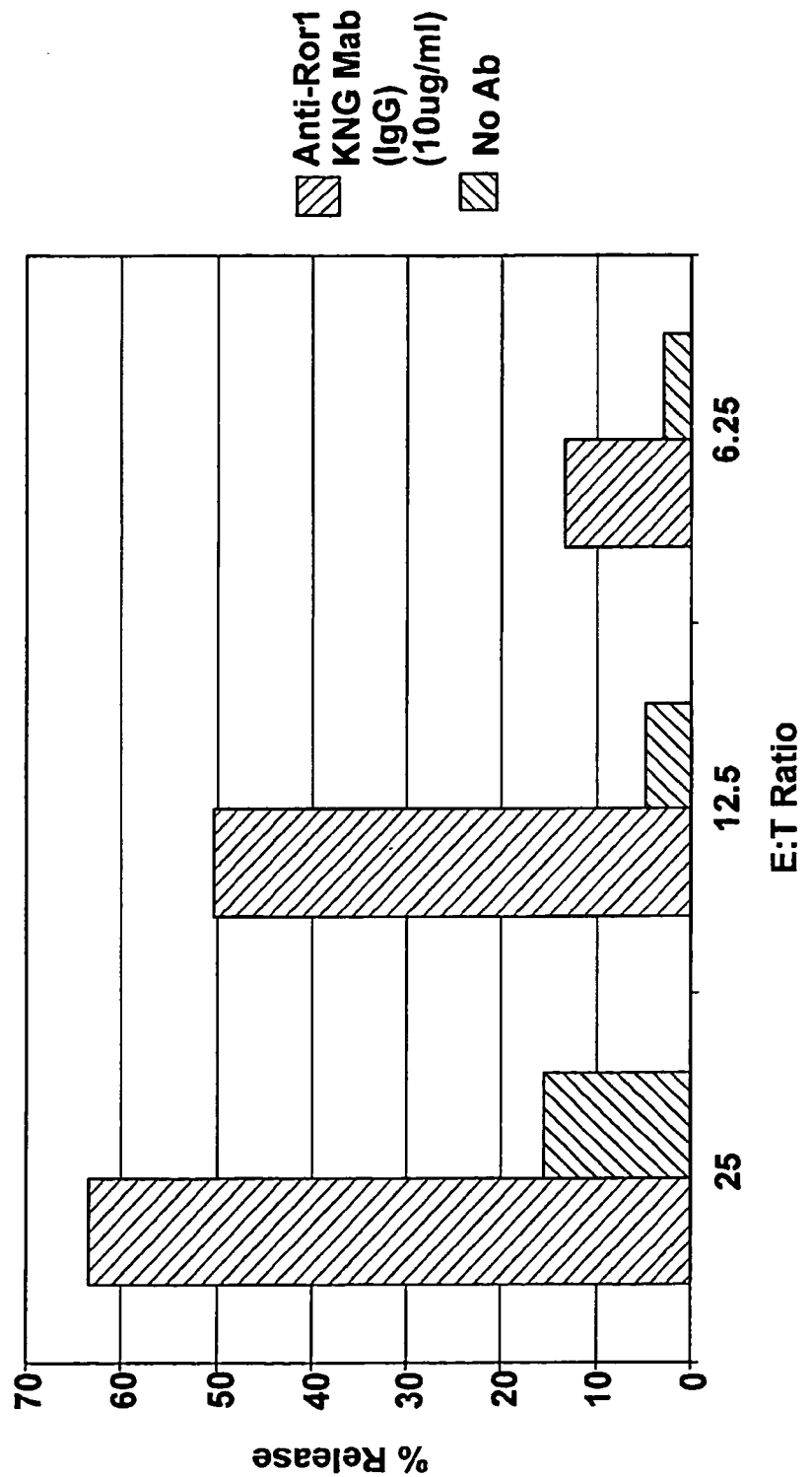

FIG. 12—Anti Rod IgG antibody induced cytotoxicity in ADCC of CLL cells.

ADCC (18 hr) using anti-Ror1 MAb and EHEB CLL cell line as target and normal healthy donor PBMC as effector cells ADCC (18 hr) using anti-Ror1 MAb and CLL cells as target and syngenic NK cells as effector cells. Results from three different patients are used FIG. 13—Anti Rod IgG antibody induces cell death of tumor cell lines originating from lung cancer (A549) and prostate cancer (DU145)

Treatment of both the A549 lung cancer cell line, and the DU145 prostate cancer cell, line with the KNG antibody and cross-linking antibody induces significant cell death compared to control antibody.

Figure 14:
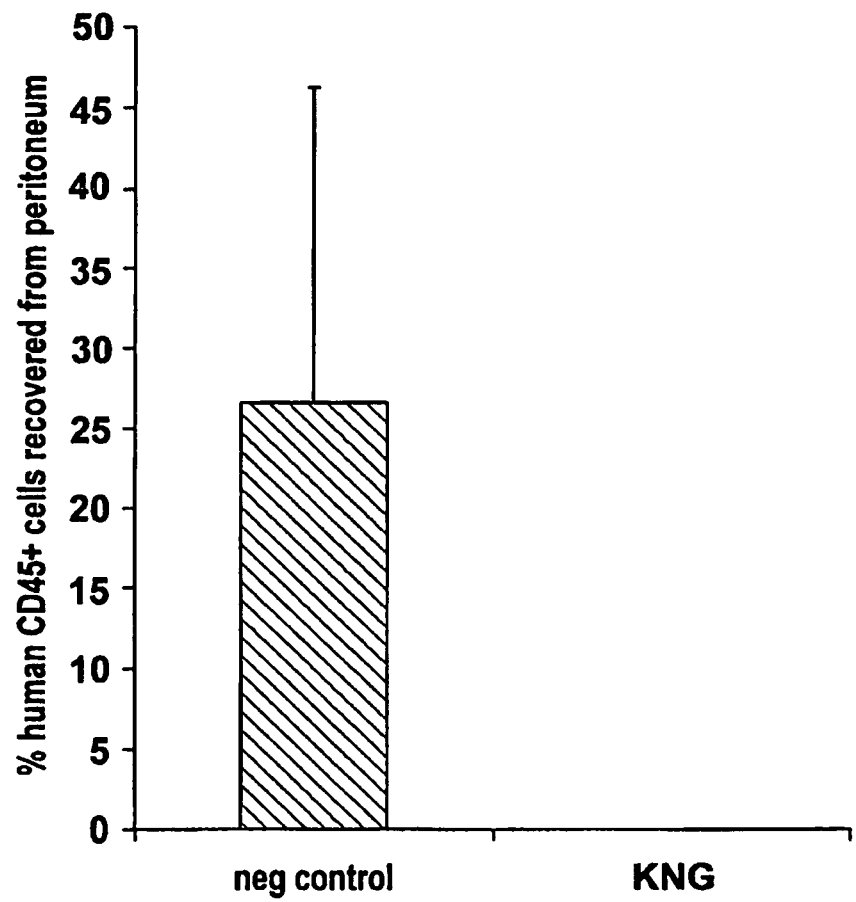

FIG. 14—In vivo treatment with anti Ror-1 IgG antibodies depletes primary CLL cells grafted into SCID mice PBMCs from a severely affected CLL patient were grafted into SCID mice. Treatment with anti-ROR MAb's totally depleted the human cells from the peritoneum of the mice.

Figure 15:
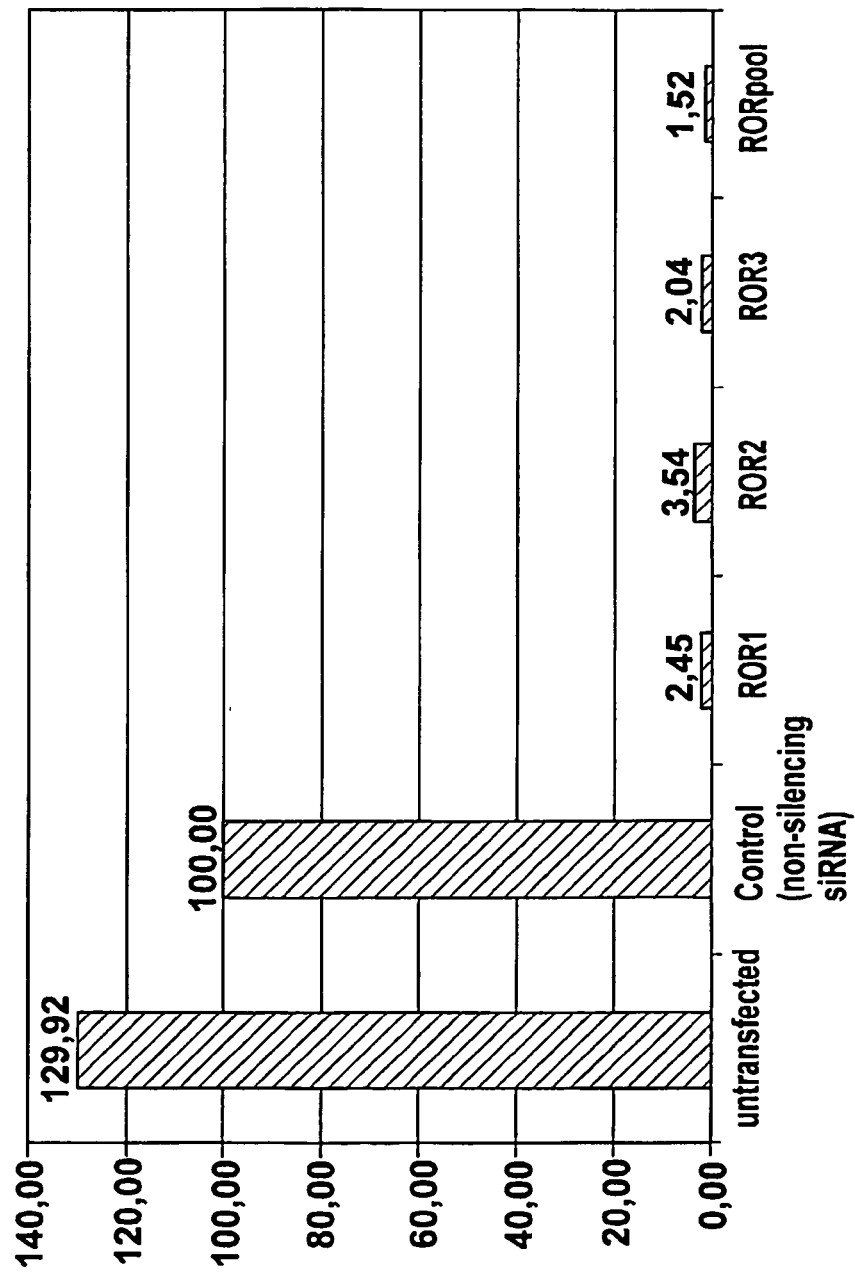

FIG. 15—siRNA downregulation of Ror-1 mRNA measured by RT-PCR in CLL siRNA mediated down regulation of Ror-1 mRNA as measured by quantitative real-time PCR in CLL cells.

Figure 16:
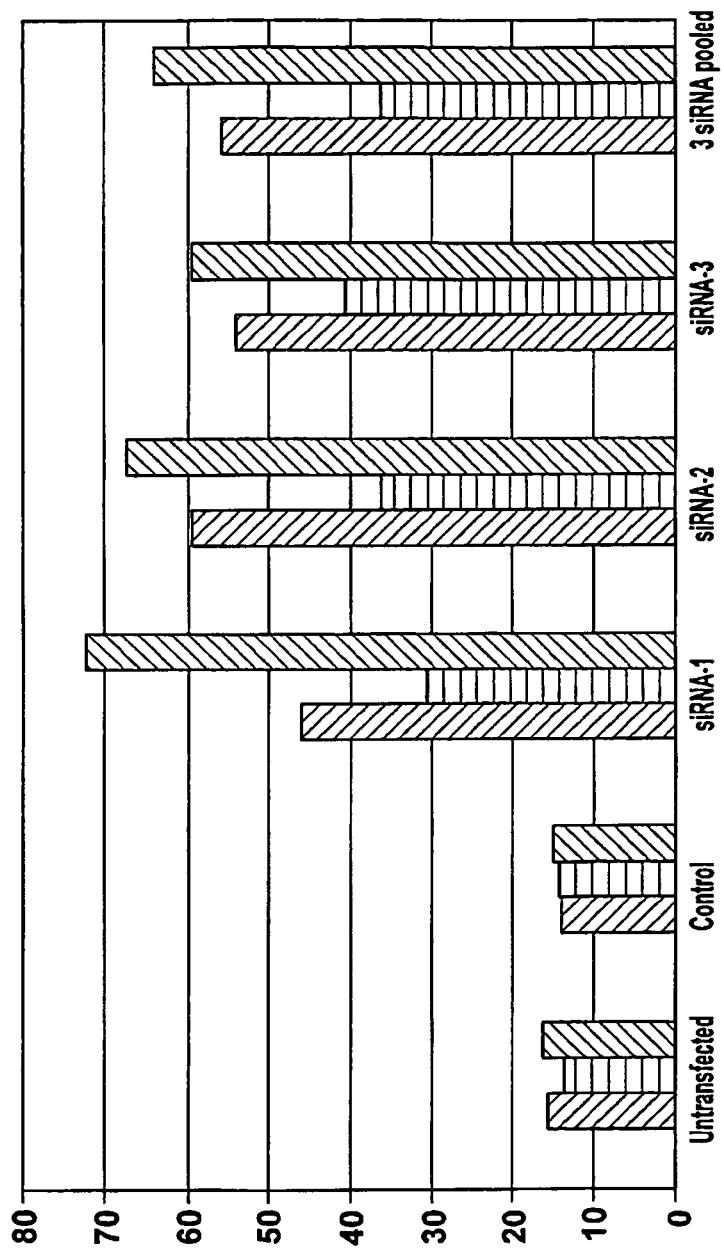

FIG. 16—siRNA silencing of Ror-1 induced Apoptosis of CLL cells siRNA mediated silencing of Ror-1 resulted in specific apoptosis of CLL cells. Results of three different patients (three different siRNA constructs were used).

FIG. 17—VL (SEQ ID NOs: 28 and 29) and VH (SEQ ID NOs: 30 and 31) sequences for Anti-Ror1 Ig24 (clone 2A4) antibody.

FIG. 18—VL (SEQ ID NOs: 32 and 33) and VH (SEQ ID NOs: 34 and 35) sequences for Anti-Ror1 CRD16 (clone 1C11) antibody.

FIG. 19—VL (SEQ ID NOs: 36 and 37) and VH (SEQ ID NOs: 38 and 39) sequences for Anti-Ror1 KNG20 (clone 4C10) antibody.

Figure 20:
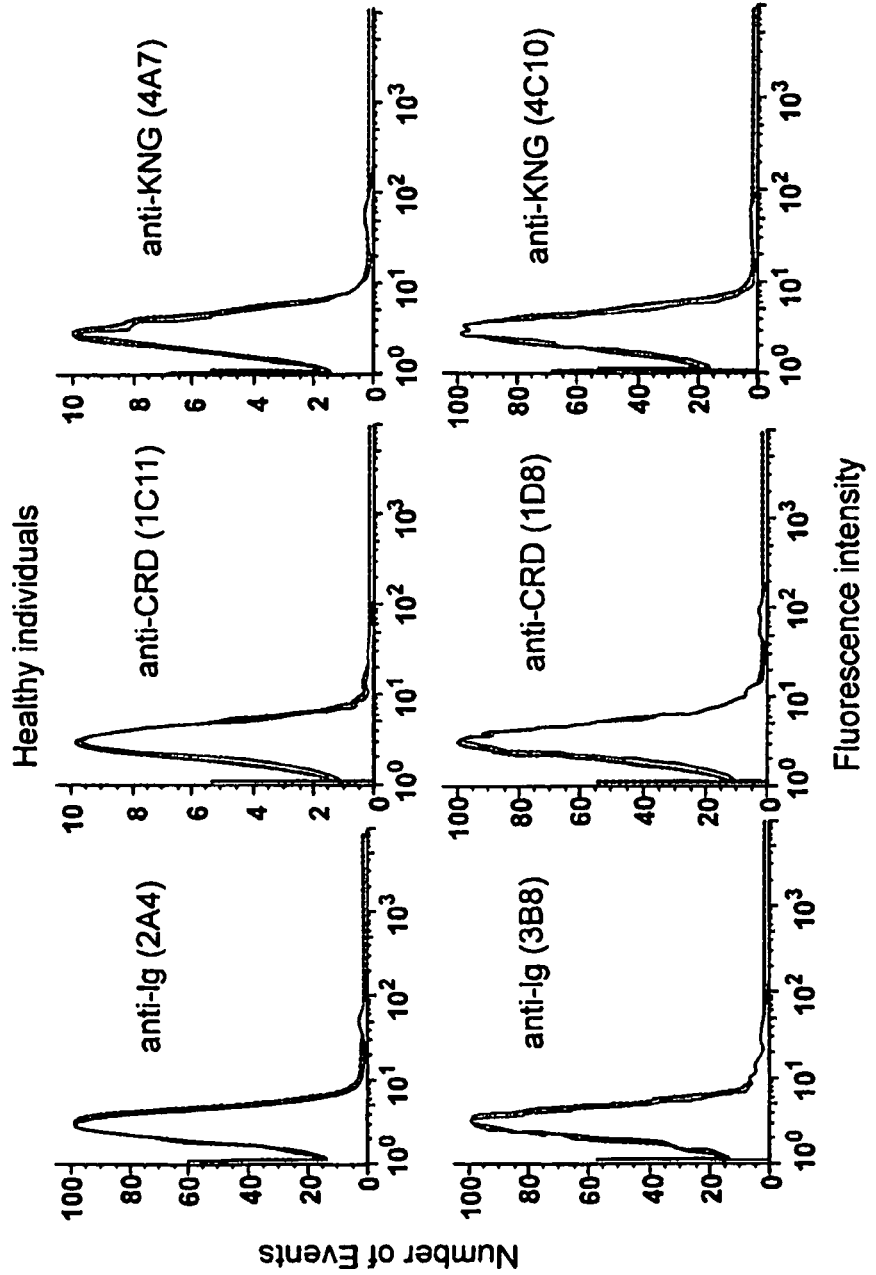

FIG. 20—Cell surface staining of PBMC of healthy donor

Conducted using six anti-ROR1 antibodies, 2A4, 1C11, 4A7, 3B8, 1D8 and 4C10.

Figure 21:
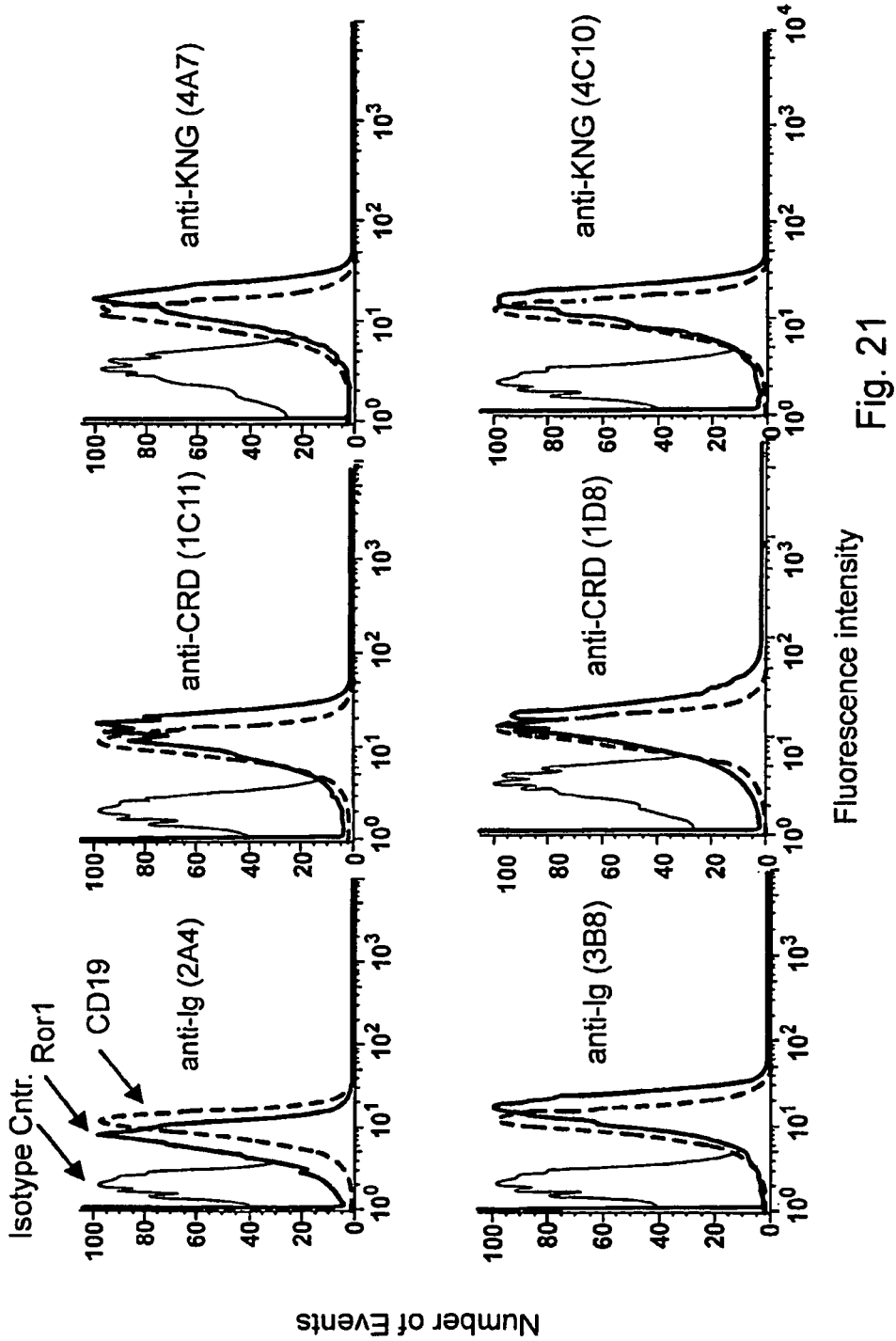

FIG. 21—Cell surface staining of CLL lymphocytes

Conducted using six anti-ROR1 antibodies, 2A4, 1C11, 4A7, 3B8, 108 and 4C10.

Figure 22:
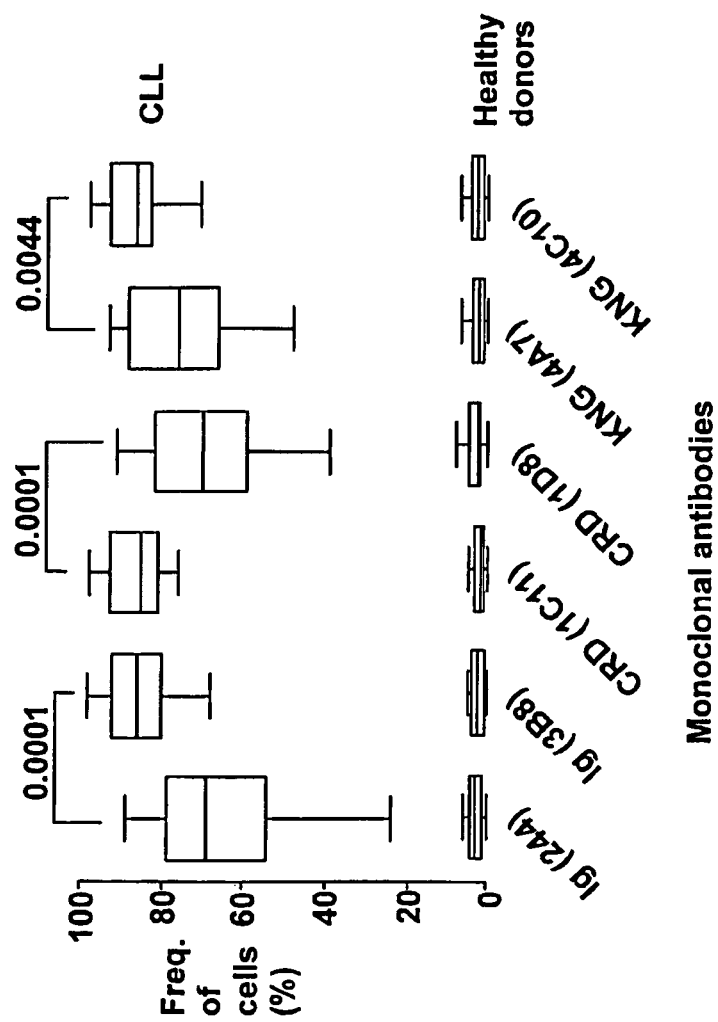
Figure 23:
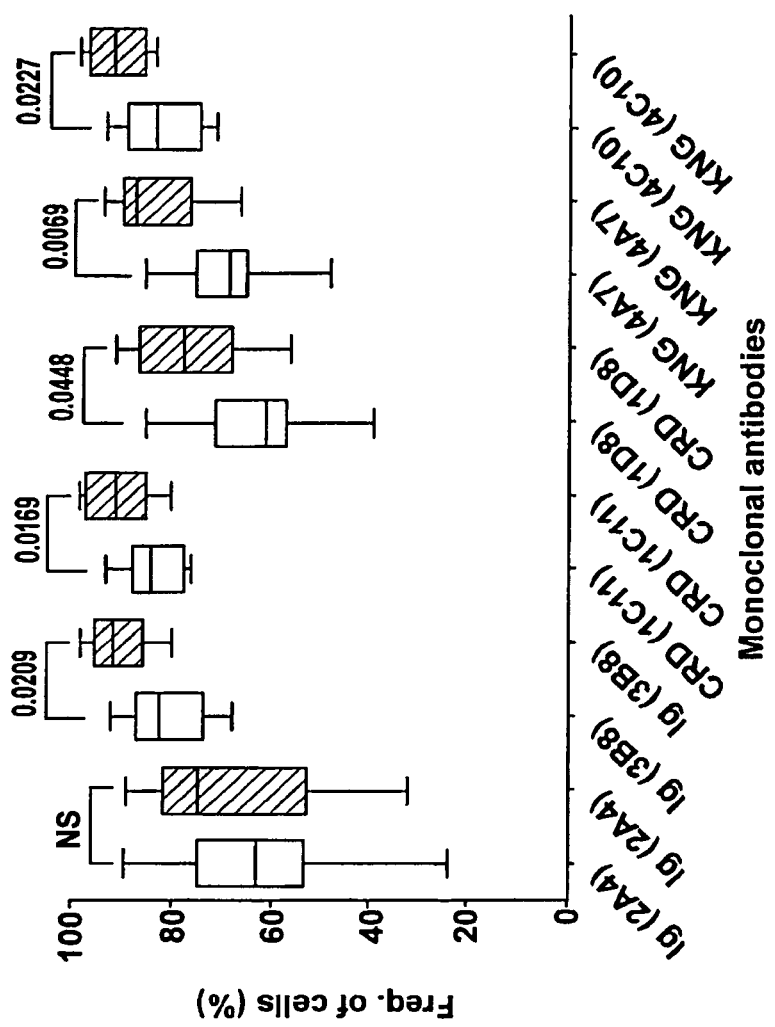
Figure 24:
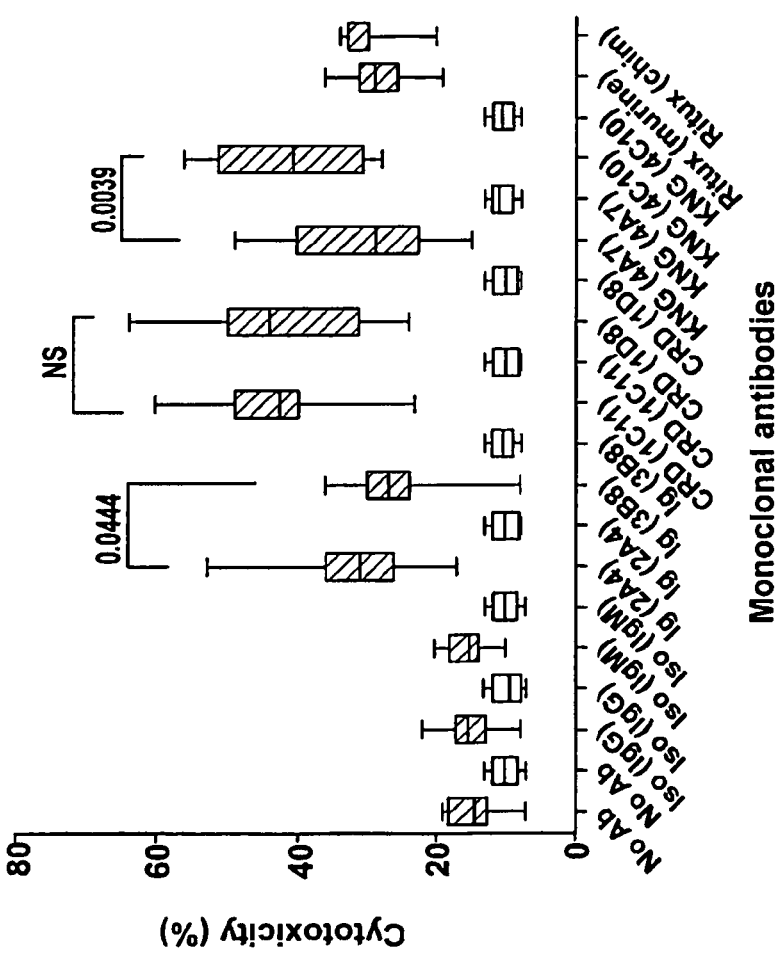

FIG. 22—Comparison of frequency of cells stained with anti-ROR1 antibodies for CLL patients and healthy donors FIG. 23—Comparison of frequency of cells stained with anti-ROR1 antibodies for progressive and non-progressive CLL disease FIG. 24—Anti-Ror1 monoclonal antibodies induced Apoptosis (Annexin-WI) of CLL cells Comparison of six anti-ROR1 antibodies, 2A4, 1C11, 4A7, 3B8, 1D8 and 4C10

Figure 25:
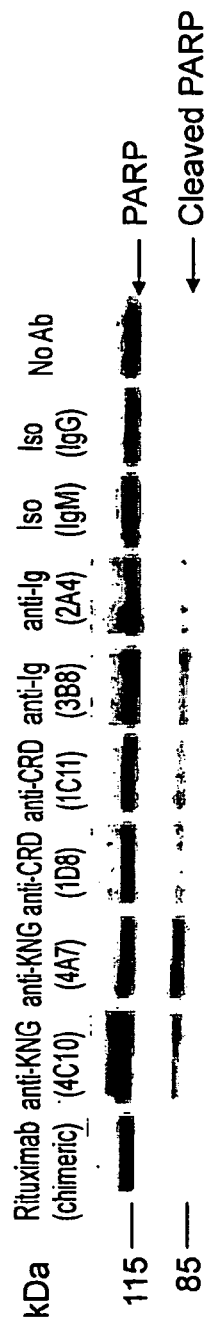

FIG. 25—PARP cleavage in CLL cells

Gel showing cleaved PARP in response to anti-ROR1 antibodies in comparison to rituximab, murine antibody and no antibody controls.

Example 1

Generation of Ror1 Specific Antibodies

Generation of Anti-Ror1 Antibodies

Mouse monoclonal antibodies were generated against four synthetic peptides depicted in Table 1. Immunograde peptides were purchased from Thermo Electron Corporation (GmbH, Ulm, Germany). Keyhole limpet hemocyanin (KLH)-conjugated peptides were used for generating mouse monoclonal antibodies (mAb) according to standard protocol with minor modifications (Kohler and Milstein C, (1975) Nature 256 pp 495-7).

The specificity of the generated monoclonal antibodies was determined by ELISA assay using irrelevant peptides and proteins as well as COS-7 cell line transfected with Ror1 gene.

TABLE 1

Ror1 peptides used for monoclonal antibody generation

| Peptide | Sequence | Location | Produced mAb class |
|---------|----------|----------|--------------------|
| Ig24 | RSTIYGSRLRIRNLDTTDTGYFQ (SEQ ID NO: 2) | 108-130 | IgM |
| CRD16 | YMESLHMQGEIENQI (SEQ ID NO: 3) | 188-202 | IgM, IgG1 |
| KNG20 | CQPWNSQYPHTHTFTALRFP (SEQ ID NO: 4) | 334-353 | IgM, IgG1 |

Preparation of Immunogenic Peptides

A peptide and KLH (Sigma) was made by mixing 1 mg of peptide with 5 mg of KLH in 1.03 ml of ionized water, thereafter, 400 µl of PBS was added to the KLH and peptide solution. After 2 min of mixing, 1.2 µl of 25% glutaraldehyde was added. The mixture was shaken for 1 hr at room temperature. The conjugated peptide was stored at −20° C. for later use. The same procedure was performed for conjugation of peptide to BSA.

To check the efficiency of conjugation, 10 µl of each peptide-KLH and peptide-BSA was mixed with 5 µl of sample buffer and boiled for 2-5 min and cooled on ice. Electrophoresis was performed using 10% SDS-PAGE gel with a mini-PROTEAN electrophoresis instrument (Bio-Rad) 100 mA for 1 hour. The gel was stained with Coomassie Blue R-250 (Sigma). The change in mobility shift of conjugated and non-conjugated KLH and BSA represents the efficiency of conjugation.

Immunization Protocol

Four BALB/c mice were used for each peptide immunization. Each mouse was immunized 5 times with an interval of two weeks. The first immunization was performed with 100 µg of peptide conjugate mixed at an 1:1 ratio with Complete Freund's Adjuvant injected intra peritoneal at a volume not exceeding 100 µl. For the subsequent immunizations, 50 µg of peptide-KLH were mixed with Incomplete Freund's Adjuvant.

One week before the last immunization, blood was collected by a vertical incision of the tail. Serum was prepared and specific antibodies were checked using ELISA. Three days before the cell fusion, 20 µg of KLH-peptide without any adjuvant was injected intravenously.

Serum ELISA

Each well was coated with 20 µg/ml of the immunizing peptide in PBS. ELISA plates were incubated at 37° C. for one hour and thereafter overnight at 4° C. Next day the plates were washed 3 times with PBS/Tween buffer for 5 min, blocked with 2.5% BSA at 37° C. for 1.5 hr and thereafter again washed ×3 with PBS/Tween buffer.

The serum was serially diluted with PBS (1:100, 1:250, 1:500, 1:1000, 1:2000). A total volume of 100 µl was added to each well and incubated at 37° C. for 1.5 hr, where after plates were washed. 100 µl of rabbit anti-mouse Ig conjugated with HRP diluted 1:1000 was used as secondary antibody. After washing 100 µl of tetramethylbenzidine (TMB) substrate was added to each well and the plates were incubated at room temperature in a dark place. After 15 min the reaction was stopped by adding 30 µl of stopping solution (0.16 M sulphuric acid) to each well. The optical density (OD) was measured at 450 nm using an ELISA reader. Mice with an adequate antibody response were ready for fusion and hybridoma generation.

Hybridoma Production

The mouse myeloma SP2/0 cell line was used for generating the hybridoma. Cells were cultured in RPMI (GIBCO) and 10% FBS until reaching to >70% confluency.

One day before cell fusion, murine BALB/C peritoneal macrophages were isolated by peritoneal lavage of 5 ml RPMI. The isolated peritoneal fluid was washed twice with RPMI. The cells were incubated in RPMI and 20% FBS for 24-48 hr at 37 C with 5% $CO_2$. Spleens of the immunized mouse were removed at sterile conditions. To acquire a single cell suspension, 10 ml of RPMI was injected to the spleen from different angles. The collected cells were washed twice with RPMI for 10 min and centrifuged at 1000 rpm.

A 50 ml sterile Falcon tube was selected and SP2/0 cells were mixed with the spleen cells at a ratio of 1:10 (1 SP2/0 and 10 spleen cells). The mixture was washed twice in RPMI. 800 µl of pre-warmed (37° C.) 50% PEG 1500 (Sigma) was added to the cell pellet slowly by mixing at the same time. Immediately after adding PEG, 20 ml of pre-warmed RPMI was added to the. The cells were washed twice at 500 rpm. Selective HAT medium was added to the pellet ($2\times10^6$ cells/ ml) and cells were seeded into a 96-well plate. Cells were incubated at 37° C. with 5% $CO_2$ and growth and colony formations were examined daily. Colonies appeared after 5-10 days. Once the colony diameter reached to 1 mm the presence of antibody against the immunized peptide was determined by ELISA. After two weeks of incubation 100 µl of supernatant from each well were collected and ELISA assay was performed using peptide alone, KLH-peptide, BSA-peptide, and KLH only as coating antigen.

Antibody Purification

The monoclonal antibodies were purified by affinity chromatography based on their isotypes. For IgG subclasses Hi-Trap Protein G Column (Pharmacia Biotech) was used. Briefly, the hybridomas were cultured in RPMI with 10% FBS and supernatants were collected every 36 hr. The supernatants were filter-sterilized (45 nm) and pH was adjusted to 7.5 bp adding 10×PBS buffer before loading to the protein G column.

The elution was performed using 0.1 mol/l glycine pH: 2.7. The pH of eluted antibody was adjusted to 7.0 with 1 mol/l Tris buffer pH: 9.0. The Eluted antibody was dialyzed with PBS pH: 7.5. The method for purification of IgM antibodies was the same as for IgG antibodies except that the affinity column was a Sepharose 4B-rabbit anti mouse IgM.

The sequences for the three monoclonal antibodies generated are found in FIGS. 17 to 19. The $V_L$ and $V_H$ sequences of the Anti-Ror1 Ig24 (clone 2A4) antibody are found in FIG. 17. The $V_L$ and $V_H$ sequences of the Anti-Ror1 CRD16 (clone 1C11) antibody are found in FIG. 19. The $V_L$ and $V_H$ sequences of the Anti-Ror1 KNG20 (clone 4C10) antibody are found in FIG. 19.

Example 2

Isolation of Cells

Patients

The World Health organisation (WHO) Classification of Neoplasms of the Haematopoietic and Lymphoid Tissues was applied (Harris N L et al., Histopathology 2000; 36:69-86). The diagnosis of CLL (n=100) was based on immunophenotyping (CD5+/CD19+/CD23+/IgM+) and the presence of >5.0×10$^9$/l lymphocytes in peripheral blood.

Patients with CLL were considered to have progressive disease according to a modification of the criteria of the NCI committee National Cancer Institute—sponsored working group guidelines for chronic lymphocytic leukaemia: revised guidelines for diagnoses and treatment. Cheson B et al, Blood 87, 4990-4997, 1996, if there was a progression during the preceding 3 months in disease-related anaemia (haemoglobin<10.0 g/dl), thrombocytopenia (<100×10$^9$/l) and/or an increase in spleen/liver/lymph-node size and/or more than a two-fold increase in the blood lymphocyte count. When these criteria were not fulfilled, the patients were considered as having non-progressive disease.

Heparinized or citrated peripheral blood or bone marrow was collected from patients with CLL and blood was also drawn from normal healthy donors (n=10). All samples were collected with informed consent and approval by the local ethics committee.

Isolation of Blood Mononuclear Cells, Granulocytes, B and T Lymphocytes

Peripheral blood mononuclear cells (PBMC) and bone marrow mononuclear cells (BMMC) were isolated using Ficoll-Hypaque (GE Healthcare, Uppsala, Sweden) density-gradient centrifugation as previously described (Rezvany M R et al., Br J Haematol 2000; 111:608-17).

Granulocytes were recovered from the top of the erythrocyte layer after Ficoll-Hypaque density-gradient centrifugation. Erythrocytes were lysed by hypo-osmosis in cold water. More than 98% of the nucleated cells were granulocytes as evaluated by immunocytology (data not shown).

Tonsil tissue was cut and passed through a metal grid and suspension of tonsil mononuclear cells was prepared by Ficoll-Hypaque density-gradient centrifugation (Rezvany M R et al., Br J Haematol 2000; 111:608-17).

T and B lymphocytes were purified from PBMC by negative selection using MACS beads (Miltenyi Biotec GmbH, Bergisch Gladbach, Germany) according to manufacturer's instruction.

Leukaemic B cells and tonsil mononuclear cells were also enriched using nylon wool purification (Rezvany M R et al., Br J Haematol 2000; 111:608-17). The purity of isolated mononuclear cells was analysed by direct immunofluorescence using conjugated monoclonal antibodies (MAb) against CD3, CD19, and CD14 (BD Biosciences, San Jose, Calif., USA) and flow cytometry (FACSCalibur BD Biosciences).

Results

PBMC of all CLL patients (n=100) as well as BMMC (n=2) expressed ROR1 at the mRNA level. ROR1 was weakly expressed also on normal tonsil B cells (2/2) but not in healthy donor PBMC (0/10), isolated normal B cells (0/6) and T cells (0/3) or enriched blood granulocytes (0/10) (Table 2).

TABLE 2

ROR1 gene expression (RT-PCR) in CLL patients and healthy control donors

| Cell source | positive cases/total analysed |
|---|---|
| CLL | |
| PMBC | 100/100 |
| BMMC | 2/2 |
| Healthy donors | |
| PBMC | 0/10 |
| T cells* | 0/3 |
| B cells* | 0/6 |
| Tonsil B cells* | 2/2 |
| Granulocytes** | 0/10 |

*Purity >90%
**purity >98%
PBMC = peripheral blood mononuclear cells,
BMMC = bone marrow mononuclear cells Example 3

RT-PCR Amplification

RT-PCR and RT-QPCR Amplification of ROR1

RT-PCR amplification was done using ROR1 specific primers (Table 3). The amplification profile included 5 min denaturation at 95° C. followed by 35 cycles of 94° C., 60° C., and 72° C. for 30 sec each, using AmpliTaq Gold DNA polymerase (Applied Biosystems, Foster City, Calif., USA).

Real-Time quantitative PCR(RT-QPCR) was performed as described earlier (Mikaelsson E et al., Blood 2005; 105:4828-35). The amplification profile included 5 min denaturation at 95° C. followed by 35 cycles of 94, 60 and 72° C. for 30 sec. each using AmpliTaq Gold DNA polymerase (Appl. Biosystems, Foster City, Calif., USA). For further details see Mikaelsson et al, Blood 105, 4828, 2005.

TABLE 3

Primers and probes used in ROR1 PCR amplifications and quantifications

| Target | Primer (5'→3') | Position | Amplicon size (bp) | Reference |
|---|---|---|---|---|
| t-Ror1 (truncated) | S: CCAAAGGACCTTCTGCAGTGGAA (P10) (SEQ ID NO: 12) | 687-709 | 450 | (10) |
| | AS: TCTCATTCCAGCACTCTGTCATGAGG (P9) (SEQ ID NO: 13) | 1111-1136 | | |
| ROR1 (RT-PCR) | S: CTGCTGCCCAAGAAACAGAG (P1) (SEQ ID NO: 14) | 455-474 | 545 | g.b. |
| | AS: CATAGTGAAGGCAGCTGTGATCT (P2) (SEQ ID NO: 15) | 977-999 | | M97675 |
| β-actin (RT-PCR) | S: ATTAAGGAGAAGCTGTGCTACGTC (SEQ ID NO: 16) | 707-730 | 215 | g.b. |
| | AS: ATGATGGAGTTGAAGGTAGTTTCG (SEQ ID NO: 17) | 898-921 | | NM_001101 |
| ROR1 (RT-QPCR) | S: AAAGAGCTACCTCTTTCTGCTGTACG (P3) (SEQ ID NO: 18) | 1771-1796 | 175 | g.b. M97675 |
| | AS: CTTCTTGTTGAAATTCCGTCCATTG (P4) (SEQ ID NO: 19) | 1921-1945 | | |
| | Probe: QCATGCTCAGCTGGTTGCTATCAAGACC9 (SEQ ID NO: 20) | 1869-1896 | | |
| β-actin (RT-QPCR) | S: CGACAGGATGCAGAAGGAGA (SEQ ID NO: 21) | 929-948 | 161 | g.b. NM_001101 |
| | AS: CGTCATACTCCTGCTTGCTG (SEQ ID NO: 22) | 1070-1089 | | |
| | Probe: QAAGATCAAGATCATTGCTCCTCCTGAG 9 (SEQ ID NO: 23) | 975-1001 | | |
| ROR1 (RT-PCR) (Extra-cellular domain) | S: ATGAATAACATCACCACGTCTCTGGGCC (P5) (SEQ ID NO: 24) | 565-592 | 1005 | g.b. |
| | AS: CTCCTTGGAATCCTTTGAATCGCA (P6) (SEQ ID NO: 25) | 1546-1569 | | M97675 |
| ROR1 (RT-PCR) (Kinase domain) | S: TTCTTCATTTGCGTCTGTCG (P7) (SEQ ID NO: 26) | 1642-1661 | 1116 | g.b. M97675 |
| | AS: CTGGCTCGGGAACATGTAAT (P8) (SEQ ID NO: 27) | 2738-2757 | | |

S = Sense,
AS = Antisense,
Q = Blue-6-FAM,
9 = TAMRA,
P1-P8 = primer number as in FIG. 1,
g.b. = genebank Results Representative RT-PCR experiments of healthy donors and CLL patients are shown in FIG. 3.

Example 4

Sequencing

Sequencing of Clonal Immunoglobulin V(D)J Rearrangements and ROR1

Amplification of the immunoglobulin V(D)J rearrangements was performed by

PCR using cDNA from PBMC, consensus VH family primers as sense and constant μ chain primer as antisense. The method has been described in detail previously (Kokhaei P et al., Exp Hematol 2007; 35:297-304; Willems P, et al., Belgium-Dutch Hematology-Oncology Group. Blood 2000; 96:63-70). The amplification included 5 min denaturation at 95° C. followed by 40 cycles at 94° C. for 30 sec, 60° C. for 30 sec and 72° C. for 30 sec using Ampli Taq Gold DNA polymerase. CH gene family-specific primers were used (see Kokhaei et al, Exp Hematol 2007, 35, 297.

Both extracellular and intracellular domains of ROR1 gene were separately amplified by RT-PCR. The amplification profile included 5 min denaturation at 95° C. followed by 35 cycles at 94, 60 and 72° C. for 30 sec each using Ampli Taq gold DNA polymerase (Mikaelsson et al, Blood 2005, 105, 4828) using cDNA of CLL patients and cloned into pGEM-T easy vector (Promega, Madison, Wis., USA) and sequenced. Extracellular domain. Sense: ATGAATAACATCAC-CACGTCTCTGGGCC (SEQ ID NO:24); anti-sense: CTC-CTTGGAATCCTTTGAATCGCA (SEQ ID NO:25). Intracellular domain sense: TTCTTCATTTGCGTCTGTCG (SEQ ID NO:26); anti-sense: CTGGCTCGGGAACATGTAAT (SEQ ID NO:27). The sequences were visually compared with the ROR1 gene (Ensembl ID; ENSG00000185483).

Sequencing of the ROR1 Gene

PBMC of CLL patients were isolated, total RNA prepared and cDNA synthesized as described above. ROR1 specific primers were designed to amplify truncated t-Ror1 (primers P9 and P10), the extracellular domains including Ig, CRD, and kringle domains (primers P5 and P6), as well as the kinase domain (primers P7 and P8). The PCR products were cloned into pGEM-T easy vector (Promega) and subjected to sequencing using T7, Sp6 and gene specific primers (Table 3).
Results Mutation analysis of cloned extracellular and cytoplasmic kinase domains of the ROR1 gene was analyzed in 10 CLL patients and showed no major genomic aberrations. Only a few point mutations (silent mutations) were found (data not shown). PCR amplification to detect a truncated ROR1 (t-Ror1) using primers P9 and P10 did not give rise to any amplicon (data not shown). Sequence for truncated Ror. Sense: CCAAAGGACCTTCTGCAGTGGAA (SEQ ID NO:12); anti-sense: TCTCATTCCAGCACTCTGTCATGAGG (SEQ ID NO:13).

Example 5

Expression of ROR1

Activation of B and T Lymphocytes of Healthy Donors and B-CLL Cells

CLL cells, isolated normal T and B cells, as well as tonsil B cells were cultured in 6-wells culture plates ($4 \times 10^6$ cells/well) in 2 ml of DMEM medium (Invitrogen, Carlsbad, Calif., USA) supplemented with 10% human AB serum, 100 U/ml penicillin, 100 μg/ml streptomycin and 2 mM L-Glutamine for 48 hours at 37° C. in humidified air with 5% CO2 and stimulated with 25 ng/ml PMA+1 μg/ml ionomycin (Sigma, St. Louis, Mo., USA).

After 48 hours of culture the cells were harvested, RNA isolated and cDNA prepared. The expression of ROR1 was analyzed by Real-Time quantitative PCR (RT-QPCR) using primers and conditions described above. 6-actin expression was used as endogenous control to quantify the ROR1 expression.

Production of Anti-Ror1 Antibodies and Specificity Testing

Rabbit anti-human Ror1 polyclonal antibodies were produced against synthetic peptides from NKSQKPYKIDSKQAS aa 904-918 of human Ror1 (designated C-Ror1-904 antibody).

Polyclonal antibodies were produced according to a modified method of Hay H (J Clin Lab Immunol 1989; 29:151-5). Rabbits less than 6 months old were injected i.m. (intramuscularly) with 125 μg of KLH-Peptide emulsified in complete to Freund's adjuvant (Sigma. St. Louis, Mo., USA). Serum samples were collected prior to injections for later titration. Booster injections (125 μg in incomplete Freund's adjuvant) were given at 2 weeks intervals. After the $4^{th}$ injection, sera were tested for the presence of anti-peptide antibodies in ELISA. Rabbits with the highest antibody titres were boosted with two additional immunizations. Sera were affinity purified using activated Sepharose 4B column (Pharmacia, Uppsala, Sweden) conjugated with peptide. The eluted antibody was dialyzed against PBS (0.15M. pH 7.2) and stored at −20° C. until use.

Immunograde peptides were purchased from Thermo Electron Corporation GmBH, Ulm, Germany. Keyhole limpet hemocyanin (KLH)-conjugated peptides were used for generating the polyclonal antibodies. The polyclonal antibodies were purified by affinity purification.

A recombinant protein representing an intracellular region of Ror1 with a molecular weight of around 70 kD (Carna Biosciences, Inc., Chuo-ku, Kobe, Japan) was used for specificity control of the C-Ror1-904 polyclonal antibody.

Briefly, the region was PCR amplified using a human full-length cDNA clone EN1031_D08 Ror1 gene (Origene Technologies, Inc., Rockville, Md., USA) as template. The PCR products were cloned into pGEM-T easy vector and subcloned into pcDNA3.1+ vector (Invitrogen) and transformed into E. coli strain Origami (Invitrogen). The integrity of the insert was verified by DNA sequencing.

After selecting an in-frame clone, the supernatant of 24 h cultured bacteria was collected and concentrated 30 times using Amicon Ultra-15 Centrifugal Filter Units (separation of polypeptides>10 kDa) (Millipore Corporation, Bedford, Mass., USA). The concentrated recombinant was subjected to Western blot and probed with anti-Ror1 antibody (goat anti-Ror1 polyclonal antibody (N-Ror1$_{com}$) (R&D systems, Inc., Minneapolis, Minn., USA)) to determine the specific reactivity.

Western Blot

The goat anti-Ror1 polyclonal antibody (N-Ror1$_{com}$) (R&D systems) as well as the antibodies produced in our lab (C-Ror1-904) were used in a Western blot.

Cells were lysed in a buffer containing 1% Triton X-100, 50 mM Tris-HCl, pH 7.4, 150 mM NaCl, 5 mM EDTA, and 1% protease inhibitor cocktail (Sigma). Protein concentration was measured by Thermo Scientific BCA Protein Assay Kit (Thermo Scientific, Rockford, Ill., USA) according to the manufacturer's instructions. Fifty micrograms of cell lysates were run on a 10% Bis-Tris SDS-PAGE gel (Invitrogen) at 120 V for 3 h under reducing conditions.

After electrophoresis, resolved proteins were transferred onto Immobilon-PVDF membranes (Millipore Corporation) in a mini Transblot cell (Invitrogen). The membranes were blocked for 1.5 h at room temperature with 5% non-fat milk in PBS plus 0.05% Tween 20 (PBS-T). All immunostainings were performed in PBS-T supplemented with 5% non-fat milk. Filters were incubated with appropriate dilutions of the anti-Ror1 antibodies over night at +4° C.

After extensive washing with PBS-T, the filters were incubated with peroxidase-conjugated goat anti-rabbit immunoglobulins (DakoCytomation, Glostrup, Denmark) for 1.5 h at room temperature followed by washing and developing with ECL chemiluminescence detection system (GE Healthcare).

Surface Staining and Flow Cytometry

Cells were analysed by flow cytometry (FACSCalibur BD Biosciences) using N-Ror1$_{com}$ (primary antibody), PE conjugated anti-CD3 (BD Biosciences, San Jose, Calif., USA), PE-Cy5-conjugated anti-CD19 (e-Bioscience, San Diego, Calif., USA), FITC-conjugated anti-CD19 (BioLegend, San Diego, Calif., USA), FITC-conjugated swine anti-goat IgG antibody (secondary antibody) (Southern biotech, Birmingham, Ala., USA) and mouse serum (blocking serum) (DakoCytomation).

Surface staining of CLL cells and normal PBMC was performed as described (Rezvany M R et al., Br J Haematol 2001; 115:263-71). Briefly, $2 \times 10^6$ cells were washed in PBS and pre-incubated with serum-free RPMI (Invitrogen), at 37° C. for 1 h followed by three washings with RPMI. One microgram of the anti-Ror1 antibody (N-Ror1$_{com}$) (R&D systems) was added and incubated at +4° C. for 30 min.

The cells were washed twice with FACS buffer (PBS, 0.1% sodium azide, and 0.5% FBS). FITC swine anti-goat IgG (1:100) (Southern biotech) was added and incubated at +4° C. for further 30 min. Blocking was performed by adding 10 μl of 10% mouse serum followed by incubation at +4° C. for 20 min. Both CD3 and CD19 antibodies were then added to the cells and incubated at +4° C. for 30 min. The cells were finally washed twice with FACS buffer and fixed by adding 1% paraformaldehyde in PBS.

The CellQuest software program (BD Biosciences) was used to determine the percentage of Ror1* cells of the CD19 population.

Results
Specificity Control of Antibodies

Affinity purified antibodies compared to a commercially available polyclonal antibody indicate that the affinity purified antibodies specifically recognize Ror1 (FIG. 7).

Expression of ROR1 in Activated Cells

Thereafter, it was analysed whether ROR1 might be induced following in vitro activation. CLL cells, normal B- and T-lymphocytes and tonsil B cells were cultured with PMA/ionomycin for 48 h to provide a strong activation signal. CLL cells and normal tonsil B cells, which constitutively expressed Ror1 mRNA, could not be further activated.

In contrast, a 15-25 fold increase in the ROR1 mRNA expression was observed in in vitro activated normal B and T cells. A representative experiment is shown in FIG. 4. The activated normal B cells also expressed Ror1 at the protein level (Western blot) (FIG. 8).

Ror1 Protein Expression

The Ror1 protein expression in CLL (n=18) was analyzed. Western blot analyses of cell lysates demonstrated in all CLL samples, the presence of two Ror1 specific bands, of 105 and an estimated of 130 kDa in size, respectively (FIG. 5).

The commercially available antibody (N-Ror1$_{com}$) seemed not to detect the estimated 130 kDa Ror1 variant.

Surface expression of Ror1 in progressive and non-progressive CLL patients are shown in FIGS. 6, 20, 21, 22 and 23 and Table 4.

The figures show that the anti-ROR1 antibodies bind preferentially to cells from CLL patients and not to cells from healthy patient. All antibodies were able to bind CLL cells but the antibodies specific for CRD appear to be of particular use. Cell surface staining for Ror1 was significantly higher in patients with progressive disease as compared to non-progressive as well as in patients with unmutated IgVH genes as compared to mutated.

TABLE 4

Protein expression of ROR1 in CLL patients (n = 18) in relation to IgVH mutational status and clinical phase.

| | | | Western blot | | | |
|---|---|---|---|---|---|---|
| Patients | Disease phase | IgVH mutation status | N-Ror1$_{com}$ (kDa) | C-Ror1-904 (kDa) | Freq. (%) of Ror1$^+$ CLL cells (CD19$^+$) | Ror1 MFI |
| CLL-1 | Non-progressive | M | 105 | 105, 130 | 80 | 13 |
| CLL-2 | Non-progressive | UM | 105 | 105, 130 | 91 | 25 |
| CLL-3 | Non-progressive | UM | 105 | 105, 130 | 36 | 10 |
| CLL-4 | Non-progressive | M | 105 | 105, 130 | 86 | 20 |
| CLL-5 | Non-progressive | UM | 105 | 105, 130 | 80 | 26 |
| CLL-6 | Non-progressive | M | 105 | 105, 130 | 91 | 35 |
| CLL-7 | Non-progressive | UM | 105 | 105, 130 | 37 | 14 |
| CLL-8 | Non-progressive | M | 105 | 105, 130 | 50 | 20 |
| CLL-9 | Non-progressive | M | 105 | 105, 130 | 69 | 20 |
| CLL-10 | Progressive | M | 105 | 105, 130 | 63 | 10 |
| CLL-11 | Progressive | M | 105 | 105, 130 | 65 | 11 |
| CLL-12 | Progressive | UM | 105 | 105, 130 | 81 | 15 |
| CLL-13 | Progressive | M | 105 | 105, 130 | 84 | 14 |
| CLL-14 | Progressive | UM | 105 | 105, 130 | 92 | 45 |
| CLL-15 | Progressive | M | 105 | 105, 130 | 61 | 19 |
| CLL-16 | Progressive | M | 105 | 105, 130 | 36 | 18 |
| CLL-17 | Progressive | M | 105 | 105, 130 | 79 | 20 |
| CLL-18 | Progressive | UM | 105 | 105, 130 | 93 | 33 |
| Mean ± SEM | | | | | 71 ± 5 | 20 ± 2 |
| Healthy controls donors (n = 10) | | | <0.1 | <0.1 | <0.1 | |

M = Mutated,
UM = Unmutated,
MFI = Mean Fluorescence Intensity

The frequency of CD19$^+$ CLL cells expressing Ror1 varied (71±5%) (mean±SEM) (range: 36-92%). There was no difference between progressive and non-progressive patients or between IgVH mutated and unmutated cases (Table 3). The mean fluorescence intensity (MFI) varied between 10 and 45 with a mean MFI value of 20. There was no statistical difference between progressive and non-progressive patients. The corresponding mean MFI of CD19 was 26 (range 9-48). Normal B cells (CD19$^+$) of healthy donors (n=10) were negative for Ror1 (<0.1%).

Example 6

SiRNA siRNA

The siRNAs used in this study were designed to target Ror-1 gene using proprietary algorithms and software available on the manufacturers website (Dharmacon, Inc. Lafayette, Colo.). Three siRNAs targeting a distinct region of the Ror-1 open reading frame were designed.

TABLE 5

Target gene: ROR1

| Target sequence (cDNA, 5' → 3') | siRNA Sequence (5' → 3') | siRNA name |
|---|---|---|
| AT GAA CCA ATG AAT AAC ATC (SEQ ID NO: 6) | AAU GAA CCA AUG AAU AAC AUC (SEQ ID NO: 7) | ROR 1 |

TABLE 5-continued

Target gene: ROR1

| Target sequence (cDNA, 5' → 3') | siRNA Sequence (5' → 3') | siRNA name |
|---|---|---|
| AAA AAT CTA TAA AGG CCA TCT (SEQ ID NO: 8) | AAA AAU CUA UAA AGG CCA UCU (SEQ ID NO: 9) | ROR 2 |
| AC ATG TCA ATT CCA AAT CAT (SEQ ID NO: 10) | AAC AUG UCA AUU CCA AAU CAU (SEQ ID NO: 11) | ROR 3 |

The three siRNAs were used independently or in combination (pool). PBMC from high-count CLL patients were plated in 48-well microwell plates at a density of 100,000 cells per well in Opti-MEM I™ Reduced-Serum Medium. Cells were transfected with the SMARTpool siRNA reagents (100 nM final concentration) using TransIT-TKO® Transfection Reagent (Mins Bio Corporation, Madison, Wis., USA) at a final concentration of 0.15 µL/well.

Untreated cells and cells transfected with the siCONTROL Non-Targeting siRNA Pool (Dharmacon) were used as negative controls. Transfection efficiency was established in prior experiments using the siGLO RISC-Free™ siRNA (Dharmacon), a fluorescently labelled non-targeting siRNA chemically modified to prevent uptake by the RISC complex. Cells were transfected for 4 hours and then transferred to monolayer cultures of NIH-3T3 fibroblasts expressing membrane-bound hCD40L. Cells were cultured for an additional 24-48 hours in RPMI+10% foetal calf serum.

Gene silencing was examined by standard RT-PCR or quantified by q-PCR using primers specific for Ror-1 (using parameters defined above). The housekeeping genes β-actin and/or RPLP0 were used for normalization. Gene expression in the cells transfected with control, non-targeting siRNA was considered to be 100% and gene expression in Ror-1 siRNA treated cells was calculated relative to the control.

siRNA or control-transfected cells were collected after 24 or 48 hours of culture and examined for apoptosis. Cells were stained with FITC-tagged Annexin V and propidium iodide (PI) and analyzed by flow cytometry. Annexin-V or PI positive or dual positive cells were considered to be apoptotic.

Results siRNA treatment of CLL cells induced a very marked down-regulation (silencing) of the Ror1 gene (FIG. 15) and apoptosis of tumour cells varying from 65-70% (FIG. 16).

Example 7

Cytotoxicity Tests

Cytotoxicity Assay Using Ror1 Monoclonal Antibodies

Frozen CLL cells were thawed and Ficoll separated to obtain live cells.

Monoclonal antibodies Ror CRD (IgM), Ror KNG (IgG1) and Ror Ig24 (IgM) were used in the assay. 10 µg/ml of antibodies were used and diluted in AIM-V medium (Invitrogen, Carlsbad, Calif., USA) (supplemented with L-glutamine, streptomycin sulphate and gentamicin sulphate) and added to a 24-well plate.

To each well $1 \times 10^6$ CLL cells were added. Cells were analysed with BD Annexin-V/PI Apoptosis assay kit (B-D) after 18 and 36 hr incubation at 37° C. using Flow Cytometry. The cells were washed twice with cold PBS and resuspended cells in binding buffer for a concentration of $1 \times 10^6$ cells/ml. 100 µl of the cell suspensions ($1 \times 10^5$ cells) was transferred to a 5 ml FACS tube. 5 µl of Annexin V-FITC and PI respectively, were added. The cells were incubated for 15 min at RT (25° C.) in the dark. 400 µl of binding buffer were added to each tube and the cells were analyzed by flow cytometry.

Antibody Dependent Cell-Mediated Cytotoxicity (ADCC) Standard Microcytotoxicity Assay $2 \times 10^6$ target cells (CLL line EHEB) were pelleted and resuspended in 100 µl of 10 mCi/ml of $^{51}$Cr per $10^6$ cells. Cells were incubated at 37° C. for 1 hour. Cells were washed three times with AIM-V medium and resuspended in AIM-V medium ($2.5 \times 10^5$/ml), 20 µl ($50 \times 10^3$) of the cell suspension was added to a 96 well V shaped-bottomed microtitre plate (Nunc, Cole-Parmer Instrument, Illinois, USA).

Varying numbers of effector cells (PBMC of healthy donor) were added in 0.1 ml volume to achieve desired effector/target (E/T) ratios of 25:1, 12.5:1 and 6.25:1.

The antibody KNG (mouse IgG1) was added with a concentration of 10 µg/ml. The antibody was diluted in AIM-V medium and was added in 0.1 ml volume to achieve a final volume of 200 µl in each well.

For spontaneous $^{51}$Cr-release control, 0.2 ml of AIM-V medium only was added to the target cells. Maximum release was determined by adding 0.2 ml of 1% NP-40. After 4, 18 and 36 hr of incubation at 37° C., the plate was centrifuged at 200×g for 5 min, and 0.1 ml of supernatant was removed for counting in a gamma counter.

Results

Antibodies against different domains of the external receptor induced cell death alone and in ADCC. The cytotoxicity of antibodies alone varied between 15-50% and in ADCC some higher killing was seen at the highest effector to target cell ratio (FIGS. 10, 11, 12, 24 and 25).

Example 8

In Vitro Effects of Anti Ror-1 mAb's on Cancer Cell Lines from Solid Tumours

The prostate cancer cell line DU145 and the lung cancer cell line A459 has previously been tested positive for Ror1 expression. Hence, work to test if treating these cell lines with anti-Ror1 MAb's could induce cell death similarly to primary CLL cells.

Cell lines were propagated in DMEM (Invitrogen) containing 10% FCS (Invitrogen). Before the experiment, cells were harvested and re-seeded at a density of 7000 cells/well together with the anti-Ror1 antibody KNG at 2 or 20 µg/ml, a control antibody at 20 µg/ml, only medium, or 3 concentrations of the cytostatic agent Paclitaxel (5, 0.5, 0.05 mg/ml) as positive control. In addition, cross linking antibodies were added as indicated at a 5 molar excess. The cells were incubated at 37° C., 5% CO2, in a humidified atmosphere for 48 h. For determining viability, a kit quantifying ATP content, which mirrors the number of metabolically active cells, hence the number of living cells, were used according to the manufacturer's instructions (CellTiter-Glo® Luminescent Cell Viability Assay, Promega).

Results

Figure 13:
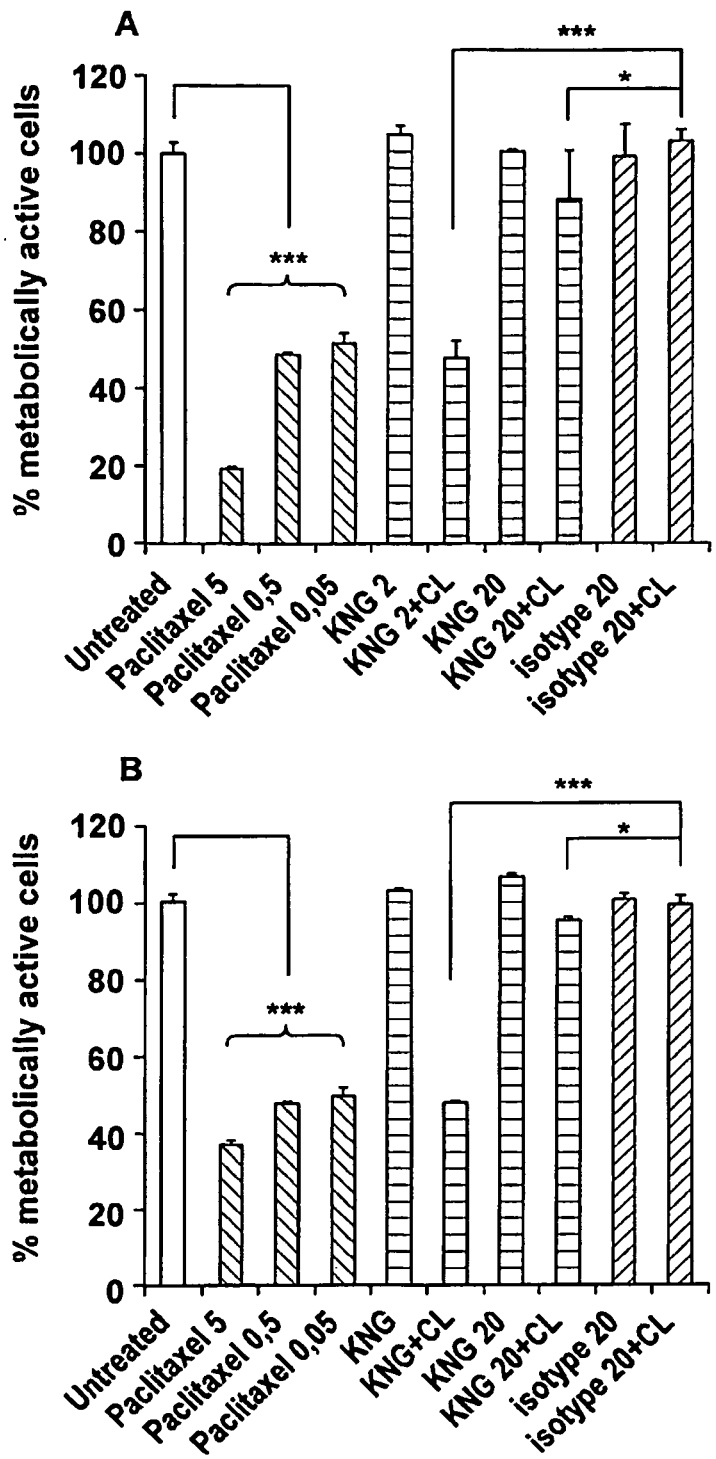

Cross linked KNG antibody induced cell death in both A549 and DU145 cell lines, FIG. 13 (A and B). The findings indicate that Ror1 is a potential target for treatment of a wide variety of cancer types.

Example 9

In Vivo Effects of Anti Ror-1 mAb's

PBMCs were isolated from peripheral blood of a severely affected CLL patient using the Ficoll Hypaque technique. The cells were stained for CD19-PE and CD5-APC (BD) to enumerate CLL cells, which was found to be around 80% of the PBMCs. In comparison, only 1.5% were T cells. In addition, the cells were stained for Ror-1 expression (FITC conjugated 1A8 antibody), which was also found on ca 80% of the cells. There after, $150 \times 10^6$ cells was injected i.p (intraperitoneally) and i.v (intravenously) into C.B.17. SCID mice. The mice were treated i.p with 10 mg/kg of two different anti-Ror mAb's, 1A8 and KNG, or irrelevant negative control mAb at day 1, 3 and 6 after transfer Mice were sacrificed day 7 and intra-peritoneal cells were collected using intra-peritoneal lavage of 8 ml PBS. Cells recovered from the peritoneum were stained for anti human CD45-FITC (BD).

Results

Both anti-ROR1 mAb's totally depleted the CLL cells from the peritoneum of injected mice (FIG. 14). This is in sharp contrast to what is observed for the control MAb and shows that treatment with anti-Ror1 specifically depletes primary human CLL cells in a xenograft in vivo model.

Example 10

ROR1 Phosphorylation

PBMC and B cells were isolated and kept on ice in 10 ml of RPMI-1640 for 10 min. Pervanadate (Sigma) stimulation was performed as previously described (Lu Y et al: J Biol Chem 2003; 278:40057). Briefly, 2 ml of 1 mM fresh pervanadate solution (1 µl $H_2O_2$+99 µl 20 mM HEPES pH: 7.4, 20 µl vanadate and 1880 µl $dH_2O$) was prepared prior to adding to the cells. Two ml of pervanadate solution was added to 10 ml RPMI-1640 medium containing the cells. Cells were incubated on ice for 1 h.

Cells were then centrifuged at 1500 rpm at 4° C. for 5 min and washed once in 1 ml ice-cold PBS. One ml of lysis buffer containing 20 mM Tris, pH 7.5, 0.5% Triton X-100, 0.15 M NaCl, 0.5% deoxycholic acid, and 10 mM EDTA was added to cell pellet. Proteinase inhibitor [1% Trasylol, 1 mM phenyl methyl sulfonyl fluoride (PMSF)] and 100 µM vanadae (Sigma) were also added to lysis buffer prior to use and incubated on ice for 10 min. Vanadate was heated at 95° C. for 5 min prior to use in lysis buffer. Cell lysates were transferred to 1.5 ml Eppendorf tubes and centrifuged at max. speed for 10 min at 4° C. Supernatants were transferred to new tubes. Immunoprecipitation was performed by adding 2-5 µg MabF3C6 antibody to the supernatant and incubation for 1 h at 4° C. with rotation.

Equal volume of protein G Sepharose (GE Healthcare, Uppsala, Sweden) and cell lysate (40:40 µl) were mixed and incubated at 4° C. overnight with rotation. The protein G Sepharose beads were washed three times with 1 ml of lysis buffer. 15 µl of reducing loading buffer was added to the beads and subjected to Western blot analysis using the PY99 antiphosphotyrosine antibody (Santa Cruz Biotechnology, CA, USA) according to the manufacturer's instruction. The N-Ror1 antibody was used for reprobing of the phosphorylated protein.

We used in the siRNA experiments leukaemic cells added to a monolayer of fibroblast transfected with CD40 L. This is a normal way to keep CLL cells alive. We have also used CD40 L stimulation of normal B cells, which did not induce is expression of Rod in normal B cells.

Results

Normal B cells did not express Ror1 while a strong non-physiologic signal (PMA ionomycin) induced Ror1 expression (FIG. 8). However, physiological stimulation (CD40L) did not seem to induce Ror1 expression in normal B-cells nor did it alter expression of Ror1 in CLL cells.

Ror1 in CLL was constitutively phosphorylated (FIG. 9) indicating that this receptor tyrosine kinase might be involved in the pathobiology of CLL. However, Ror protein expression induced in normal B cells was not phosphorylated (FIG. 8).

Example 11

Preferred Pharmaceutical Formulations and Modes and Doses of Administration

The polypeptides, polynucleotides and antibodies of the present invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The polypeptides, polynucleotides and antibodies of the present invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for administration. A device which delivers a pulsed electric field to cells increases the permeability of the cell membranes to the drug, resulting in a significant enhancement of intracellular drug delivery.

Polypeptides, polynucleotides and antibodies of the invention can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of administration is the ReGel injectable system that is thermosensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Polypeptides, polynucleotides and antibodies of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient (Derossi et al., 1998, *Trends Cell Biol.*, 8, 84-87).

Preferably, the pharmaceutical formulation of the present invention is a unit dosage containing a daily dose or unit, daily sub-dose or an appropriate fraction thereof, of the active ingredient.

The polypeptides, polynucleotides and antibodies of the invention can be administered by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the polypeptides, polynucleotides and antibodies of the invention can be administered alone but will generally be administered in admixture with a suitable pharmaceutical excipient diluent or carrier selected with regard to the intended route of administration and standard pharmaceutical practice.

The polypeptides, polynucleotides and antibodies of the invention can also be administered parenterally, for example, intravenously, intra-arterially, intraperitoneally, intra-thecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Generally, in humans, oral or parenteral administration of the polypeptides, polynucleotides and antibodies of the invention is the preferred route, being the most convenient.

For veterinary use, the polypeptides, polynucleotides and antibodies of the invention are administered as a suitably acceptable formulation in accordance with normal veterinary practice and the veterinary surgeon will determine the dosing regimen and route of administration which will be most appropriate for a particular animal.

The formulations of the pharmaceutical compositions of the invention may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Preferred unit dosage formulations are those containing a daily dose or unit, daily sub-dose or an appropriate fraction thereof, of an active ingredient.

A preferred delivery system of the invention may comprise a hydrogel impregnated with a polypeptides, polynucleotides and antibodies of the invention, which is preferably carried on a tampon which can be inserted into the cervix and withdrawn once an appropriate cervical ripening or other desirable affect on the female reproductive system has been produced.

It should be understood that in addition to the ingredients particularly mentioned above the formulations of this invention may include other agents conventional in the art having regard to the type of formulation in question.

Example 12

Exemplary Pharmaceutical Formulations

Whilst it is possible for a polypeptides, polynucleotides and antibodies of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Typically, the carriers will be water or saline which will be sterile and pyrogen-free.

The following examples illustrate pharmaceutical formulations according to the invention in which the active ingredient is a polypeptides, polynucleotides and/or antibody of the invention.

Example 12A

Injectable Formulation

| | |
|---|---|
| Active ingredient | 0.200 g |
| Sterile, pyrogen free phosphate buffer (pH7.0) to | 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example 12B

Intramuscular Injection

| | |
|---|---|
| Active ingredient | 0.20 g |
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

The invention claimed is:

1. A biological inhibitor of ROR1 capable of inducing cell death in a cell expressing ROR1,
wherein the inhibitor is a monoclonal antibody, and wherein the extracellular domain to which the antibody binds has an amino acid sequence selected from the group consisting of YMESLHMQGEIENQI (SEQ ID NO: 3), CQPWNSQYPHTHTFTALRFP (SEQ ID NO: 4) and RSTIYGSRLRIRNLDTTDTGYFQ (SEQ ID NO: 2).

2. A pharmaceutical composition comprising a biological inhibitor of claim 1 and a pharmaceutically acceptable excipient, diluent or carrier.

3. A pharmaceutical composition as claimed in claim 2 which induces cell death in a cell expressing ROR1.

4. A kit of parts comprising:
(i) a biological inhibitor as claimed in claim 1;
(ii) apparatus for administering the biological inhibitor; and
(iii) instructions for use.

5. The biological inhibitor of claim 1, wherein the $V_H$ and $V_L$ regions of the antibody consist of the amino acid sequences shown in any one of FIGS. 17, 18 and 19 (SEQ ID NO:29 and SEQ ID NO: 31, SEQ ID NO: 33 and SEQ ID NO: 35, or SEQ ID NO: 37 and SEQ ID NO:39).

* * * * *